US008561164B2

(12) United States Patent
Ellis, III

(10) Patent No.: US 8,561,164 B2
(45) Date of Patent: *Oct. 15, 2013

(54) COMPUTERS AND MICROCHIPS WITH A SIDE PROTECTED BY AN INTERNAL HARDWARE FIREWALL AND AN UNPROTECTED SIDE CONNECTED TO A NETWORK

(76) Inventor: Frampton E. Ellis, III, Arlington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/829,120

(22) Filed: Jul. 1, 2010

(65) Prior Publication Data
US 2011/0004931 A1 Jan. 6, 2011

Related U.S. Application Data

(63) Continuation of application No. 10/663,911, filed on Sep. 17, 2003, now Pat. No. 7,814,233, which is a continuation of application No. 09/213,875, filed on Dec. 17, 1998, now Pat. No. 6,725,250, which is a continuation-in-part of application No. 08/980,058, filed on Nov. 26, 1997, now Pat. No. 6,732,141, and a continuation-in-part of application No. PCT/US97/21812, filed on Nov. 28, 1997, and a continuation-in-part of application No. 08/980,058, filed on Nov. 26, 1997, now Pat. No. 6,732,141.

(60) Provisional application No. 60/068,366, filed on Dec. 19, 1997, provisional application No. 60/066,415, filed on Nov. 24, 1997, provisional application No. 60/066,313, filed on Nov. 21, 1997, provisional application No. 60/033,871, filed on Dec. 20, 1996, provisional application No. 60/032,207, filed on Dec. 2, 1996, provisional application No. 60/031,855, filed on Nov. 29, 1996.

(51) Int. Cl.
*G06F 15/16* (2006.01)
*G06F 7/04* (2006.01)

(52) U.S. Cl.
USPC .................. 726/11; 709/250; 712/28; 712/32; 726/3

(58) Field of Classification Search
USPC ........... 709/200, 201, 250; 712/28, 32; 726/3, 726/11
See application file for complete search history.

(56) References Cited

U.S. PATENT DOCUMENTS 3,539,876 A 11/1970 Feinberg et al.
(Continued)

FOREIGN PATENT DOCUMENTS

DE 40 08 335 9/1991
(Continued)

OTHER PUBLICATIONS

Force, G.; "Portable data encryption approaches". WESCON/95. Conference record. "Microelectronics Communication Technology Producing Quality Productions Mobile and Portable Power Emerging Technologies", Date: Nov. 7-8, 1995; pp. 413-419. [retrieved from IEEE database Nov. 15, 2010].*

(Continued)

*Primary Examiner* — Saleh Najjar
*Assistant Examiner* — Lashanya Nash
(74) *Attorney, Agent, or Firm* — DLA Piper LLP (US)

(57) ABSTRACT

A computer or microchip including one or more microprocessors or processing units, at least one network communication component, and an internal hardware firewall, located on a microchip and configured to separate a protected side of the computer or microchip from an unprotected side of the computer or microchip, the unprotected side being configured to connect to a network. The hardware protected side of the computer or microchip includes at least one microprocessor or processing unit. The unprotected network side of the computer or microchip is located between the internal hardware firewall and the network and includes the at least one unprotected microprocessors or processing units and network communications components. The unprotected microprocessors or processing units and network communications components are separate components and both are separate from the internal hardware firewall. The computer or microchip can be actively configured, including using microchips with field programmable gate arrays.

61 Claims, 8 Drawing Sheets

(56) References Cited

U.S. PATENT DOCUMENTS

| | | | |
|---|---|---|---|
| 3,835,530 A | 9/1974 | Kilby | |
| 4,245,306 A * | 1/1981 | Besemer et al. | 709/245 |
| 4,276,594 A | 6/1981 | Morley | |
| 4,278,837 A | 7/1981 | Best | |
| 4,467,400 A | 8/1984 | Stopper | |
| 4,489,397 A | 12/1984 | Lee | |
| 4,703,436 A | 10/1987 | Varshney | |
| 4,736,317 A | 4/1988 | Hu et al. | |
| 4,747,139 A | 5/1988 | Taaffe | |
| 4,827,508 A | 5/1989 | Shear | |
| 4,855,903 A | 8/1989 | Carleton et al. | |
| 4,893,174 A | 1/1990 | Yamada et al. | |
| 4,907,228 A | 3/1990 | Bruckert et al. | |
| 4,918,596 A | 4/1990 | Nakano | |
| 4,969,092 A | 11/1990 | Shorter | |
| 5,025,369 A | 6/1991 | Schwartz | |
| 5,031,089 A | 7/1991 | Liu et al. | |
| 5,068,780 A | 11/1991 | Bruckert et al. | |
| 5,103,393 A | 4/1992 | Harris et al. | |
| 5,109,329 A | 4/1992 | Strelioff | |
| 5,109,512 A | 4/1992 | Bahr et al. | |
| 5,136,708 A | 8/1992 | LaPourtre et al. | |
| 5,155,808 A | 10/1992 | Shimizu | |
| 5,195,031 A | 3/1993 | Ordish | |
| 5,212,780 A | 5/1993 | Padgaonkar et al. | |
| 5,214,657 A | 5/1993 | Farnworth et al. | |
| 5,237,507 A | 8/1993 | Chasek | |
| 5,260,943 A | 11/1993 | Comroe et al. | |
| 5,282,272 A | 1/1994 | Guy et al. | |
| 5,283,819 A | 2/1994 | Glick et al. | |
| 5,291,494 A | 3/1994 | Bruckert et al. | |
| 5,291,502 A | 3/1994 | Pezeshki et al. | |
| 5,291,505 A | 3/1994 | Nielsen | |
| 5,341,477 A | 8/1994 | Pitkin et al. | |
| 5,349,682 A | 9/1994 | Rosenberry | |
| 5,357,404 A | 10/1994 | Bright et al. | |
| 5,357,632 A | 10/1994 | Pian et al. | |
| 5,361,362 A | 11/1994 | Benkeser et al. | |
| 5,381,534 A | 1/1995 | Shi | |
| 5,388,211 A | 2/1995 | Hornbuckle | |
| 5,392,400 A | 2/1995 | Berkowitz et al. | |
| 5,410,651 A | 4/1995 | Sekizawa et al. | |
| 5,426,741 A | 6/1995 | Butts, Jr. et al. | |
| 5,428,783 A | 6/1995 | Lake | |
| 5,434,998 A | 7/1995 | Akai | |
| 5,446,843 A | 8/1995 | Fucito et al. | |
| 5,457,797 A | 10/1995 | Butterworth et al. | |
| 5,475,606 A | 12/1995 | Muyshondt et al. | |
| 5,497,465 A * | 3/1996 | Chin et al. | 710/100 |
| 5,515,511 A | 5/1996 | Nguyen et al. | |
| 5,522,070 A | 5/1996 | Sumimoto | |
| 5,530,949 A | 6/1996 | Koda | |
| 5,535,408 A | 7/1996 | Hillis | |
| 5,546,594 A | 8/1996 | Wazumi | |
| 5,550,984 A * | 8/1996 | Gelb | 709/245 |
| 5,568,375 A | 10/1996 | Rausch | |
| 5,570,270 A | 10/1996 | Naedel et al. | |
| 5,572,643 A | 11/1996 | Judson | |
| 5,576,554 A | 11/1996 | Hsu | |
| 5,586,121 A | 12/1996 | Moura et al. | |
| 5,587,928 A | 12/1996 | Jones et al. | |
| 5,588,003 A | 12/1996 | Ohba et al. | |
| 5,590,284 A | 12/1996 | Crosetto | |
| 5,592,376 A | 1/1997 | Hodroff | |
| 5,592,632 A | 1/1997 | Leung et al. | |
| 5,594,491 A | 1/1997 | Hodge et al. | |
| 5,600,597 A * | 2/1997 | Kean et al. | 365/189.08 |
| 5,604,882 A | 2/1997 | Hoover et al. | |
| 5,606,615 A | 2/1997 | LaPointe et al. | |
| 5,608,448 A | 3/1997 | Smoral et al. | |
| 5,615,127 A | 3/1997 | Beatty et al. | |
| 5,627,879 A | 5/1997 | Russell et al. | |
| 5,666,484 A | 9/1997 | Orimo et al. | |
| 5,678,028 A | 10/1997 | Bershteyn et al. | |
| 5,680,461 A | 10/1997 | McManis | |
| 5,680,548 A | 10/1997 | Trugman | |
| 5,696,902 A | 12/1997 | Leclercq et al. | |
| 5,699,528 A | 12/1997 | Hogan | |
| 5,701,507 A | 12/1997 | Bonneau, Jr. et al. | |
| 5,710,884 A | 1/1998 | Dedrick | |
| 5,734,913 A | 3/1998 | Iwamura et al. | |
| 5,748,489 A | 5/1998 | Beatty et al. | |
| 5,752,067 A | 5/1998 | Wilkinson et al. | |
| 5,754,766 A * | 5/1998 | Shaw et al. | 709/200 |
| 5,758,077 A | 5/1998 | Danahy et al. | |
| 5,758,345 A | 5/1998 | Wang | |
| 5,761,507 A | 6/1998 | Govett | |
| 5,764,889 A | 6/1998 | Ault et al. | |
| 5,774,337 A | 6/1998 | Lee et al. | |
| 5,774,668 A | 6/1998 | Choquier et al. | |
| 5,774,721 A | 6/1998 | Robinson | |
| 5,784,551 A | 7/1998 | De Leva et al. | |
| 5,784,628 A | 7/1998 | Reneris | |
| 5,790,431 A | 8/1998 | Ahrens, Jr. et al. | |
| 5,793,968 A | 8/1998 | Gregerson et al. | |
| 5,794,059 A | 8/1998 | Barker et al. | |
| 5,802,320 A | 9/1998 | Baehr et al. | |
| 5,809,190 A | 9/1998 | Chen | |
| 5,815,665 A | 9/1998 | Teper et al. | |
| 5,815,793 A | 9/1998 | Ferguson | |
| 5,826,014 A | 10/1998 | Coley et al. | |
| 5,826,029 A | 10/1998 | Gore | |
| 5,828,833 A | 10/1998 | Belville et al. | |
| 5,835,726 A | 11/1998 | Shwed et al. | |
| 5,838,436 A | 11/1998 | Hotaling et al. | |
| 5,838,542 A | 11/1998 | Nelson et al. | |
| 5,843,799 A | 12/1998 | Hsu et al. | |
| 5,844,594 A | 12/1998 | Ferguson | |
| 5,845,074 A | 12/1998 | Kobata | |
| 5,850,449 A | 12/1998 | McManis | |
| 5,861,817 A | 1/1999 | Palmer et al. | |
| 5,862,357 A | 1/1999 | Hagersten et al. | |
| 5,864,738 A | 1/1999 | Kessler et al. | |
| 5,870,721 A | 2/1999 | Norris | |
| 5,872,987 A * | 2/1999 | Wade et al. | 712/3 |
| 5,881,284 A | 3/1999 | Kubo | |
| 5,889,989 A * | 3/1999 | Robertazzi et al. | 718/105 |
| 5,896,499 A * | 4/1999 | McKelvey | 726/11 |
| 5,905,429 A | 5/1999 | Hornstein et al. | |
| 5,909,052 A | 6/1999 | Ohta et al. | |
| 5,909,681 A | 6/1999 | Passera et al. | |
| 5,917,629 A | 6/1999 | Hortensius et al. | |
| 5,919,247 A | 7/1999 | Van Hoff et al. | |
| 5,930,511 A | 7/1999 | Hinsley | |
| 5,943,421 A * | 8/1999 | Grabon | 380/269 |
| 5,964,832 A | 10/1999 | Kisor | |
| 5,978,829 A | 11/1999 | Chung et al. | |
| 6,003,133 A | 12/1999 | Moughanni et al. | |
| 6,052,555 A | 4/2000 | Ferguson | |
| 6,065,118 A | 5/2000 | Bull et al. | |
| 6,067,082 A | 5/2000 | Enmei | |
| 6,073,209 A | 6/2000 | Bergsten | |
| 6,078,733 A | 6/2000 | Osborne | |
| 6,093,933 A | 7/2000 | Farnworth et al. | |
| 6,098,091 A | 8/2000 | Kisor | |
| 6,112,225 A | 8/2000 | Kraft et al. | |
| 6,112,243 A | 8/2000 | Downs et al. | |
| 6,115,698 A | 9/2000 | Tuck et al. | |
| 6,167,428 A | 12/2000 | Ellis | |
| 6,202,153 B1 | 3/2001 | Diamant et al. | |
| 6,208,634 B1 | 3/2001 | Boulos et al. | |
| 6,219,627 B1 | 4/2001 | Bonneau et al. | |
| 6,268,788 B1 | 7/2001 | Gray | |
| 6,287,949 B1 | 9/2001 | Mori et al. | |
| 6,326,245 B1 | 12/2001 | Farnworth et al. | |
| 6,366,472 B2 | 4/2002 | Alina et al. | |
| 6,440,775 B2 | 8/2002 | Khoury | |
| 6,645,832 B2 | 11/2003 | Kim et al. | |
| 6,725,250 B1 | 4/2004 | Ellis, III | |
| 6,732,141 B2 | 5/2004 | Ellis | |
| 6,772,347 B1 | 8/2004 | Xie et al. | |
| 6,797,545 B2 | 9/2004 | Farnworth et al. | |
| 6,950,947 B1 | 9/2005 | Purtell et al. | |
| 7,024,449 B1 | 4/2006 | Ellis, III | |

(56) References Cited

U.S. PATENT DOCUMENTS

| | | | |
|---|---|---|---|
| 7,035,906 | B1 | 4/2006 | Ellis, III |
| 7,047,275 | B1 | 5/2006 | Ellis |
| 7,148,565 | B2 | 12/2006 | Kim et al. |
| 7,161,175 | B2 | 1/2007 | Shau |
| 7,412,588 | B2 * | 8/2008 | Georgiou et al. ............... 712/33 |
| 7,467,406 | B2 | 12/2008 | Cox et al. |
| 7,506,020 | B2 | 3/2009 | Ellis |
| 7,562,211 | B2 | 7/2009 | Paya et al. |
| 7,606,854 | B2 | 10/2009 | Ellis, III |
| 7,634,529 | B2 | 12/2009 | Ellis, III |
| 7,805,756 | B2 | 9/2010 | Ellis |
| 7,814,233 | B2 | 10/2010 | Ellis |
| 7,840,997 | B2 | 11/2010 | Shevchenko |
| 7,908,650 | B2 | 3/2011 | Ellis |
| 7,926,097 | B2 | 4/2011 | Ellis |
| 7,984,301 | B2 | 7/2011 | Kaabouch et al. |
| 8,010,789 | B2 | 8/2011 | Witchey |
| 8,125,796 | B2 | 2/2012 | Ellis |
| 8,164,170 | B2 | 4/2012 | Ellis |
| 8,171,537 | B2 | 5/2012 | Ellis |
| 8,209,373 | B2 | 6/2012 | Ellis |
| 8,255,986 | B2 | 8/2012 | Ellis |
| 8,291,485 | B2 | 10/2012 | Ellis |
| 8,312,529 | B2 | 11/2012 | Ellis |
| 8,378,474 | B2 | 2/2013 | Ellis |
| 2001/0046119 | A1 | 11/2001 | Hamano et al. |
| 2001/0054159 | A1 | 12/2001 | Hoshino |
| 2004/0073603 | A1 | 4/2004 | Ellis |
| 2004/0098621 | A1 | 5/2004 | Raymond |
| 2004/0158744 | A1 | 8/2004 | Deng et al. |
| 2004/0162992 | A1 | 8/2004 | Sami et al. |
| 2004/0215931 | A1 | 10/2004 | Ellis |
| 2005/0138169 | A1 | 6/2005 | Bahr |
| 2005/0180095 | A1 | 8/2005 | Ellis |
| 2006/0075001 | A1 | 4/2006 | Canning et al. |
| 2006/0095497 | A1 | 5/2006 | Ellis |
| 2006/0177226 | A1 | 8/2006 | Ellis |
| 2006/0190565 | A1 | 8/2006 | Ellis |
| 2006/0248749 | A1 | 11/2006 | Ellis |
| 2007/0162974 | A1 | 7/2007 | Speidel |
| 2007/0196948 | A1 | 8/2007 | Trezza |
| 2007/0300305 | A1 | 12/2007 | Gonsalves et al. |
| 2008/0083976 | A1 | 4/2008 | Haba et al. |
| 2008/0134290 | A1 | 6/2008 | Olsson |
| 2009/0026524 | A1 | 1/2009 | Kreupl et al. |
| 2009/0031412 | A1 | 1/2009 | Ellis |
| 2009/0200661 | A1 | 8/2009 | Ellis |
| 2009/0254986 | A1 | 10/2009 | Harris et al. |
| 2009/0282092 | A1 | 11/2009 | Ellis |
| 2010/0011083 | A1 | 1/2010 | Ellis |
| 2011/0004930 | A1 | 1/2011 | Ellis |
| 2011/0004931 | A1 | 1/2011 | Ellis |
| 2011/0225645 | A1 | 9/2011 | Ellis |
| 2012/0096537 | A1 | 4/2012 | Ellis |
| 2012/0155002 | A1 | 6/2012 | Ellis |
| 2012/0175752 | A1 | 7/2012 | Ellis |

FOREIGN PATENT DOCUMENTS

| | | |
|---|---|---|
| EP | 0 647 052 | 4/1995 |
| EP | 0 840216 | 5/1998 |
| EP | 0 853 279 | 7/1998 |
| EP | 1 164 766 | 12/2011 |
| WO | WO 94/01964 | 1/1994 |
| WO | WO 95/01060 | 1/1995 |
| WO | WO 98/26366 | 6/1998 |
| WO | WO 99/04561 | 1/1999 |
| WO | WO 99/32972 | 7/1999 |
| WO | WO 2011/094616 | 8/2011 |
| WO | WO 2011/103299 | 8/2011 |

OTHER PUBLICATIONS

A. D. Roming, P.V. Dressendor, and D.W. Palmer, "High Performance microsystem packaging: A perspective", Microelecton. Rel., vol. 37, pp. 1771-1781, Oct./Nov. 1997 [retrieved from ScienceDirect database on Nov. 15, 2010].*

Kayassi, A; L.; Ferzil, R.; Fawaz, M; "FPGA-based Internet protocol firewall chip", Electronics, Circuits and Systems, 2000. ICECS 2000. The 7th IEEE International Conference on vol. 1, Dec. 17-20, 2000 pp. 316-319 vol. 1[retrieved from IEEE database Nov. 15, 2010].*

Litzkow, et al., "Condor—A Hunter of Idle Workstations", 1988 IEEE, pp. 104-111.

Theimer, et al., "Finding Idle Machines in a Workstation-Based Distributed System", IEEE Transactons on Software Engineering, Nov. 1989; vol. 15, 11, pp. 1444-1458.

Brown et al., Special Edition Using Netscape TM 2 Second Edition, Que Corporation, 1995, Ch. 1-2.

Gilder, "Angst and Awe on the Internet by George Gilder", Forbes ASAP, Dec. 4. 1995.

Tandiary, et al., "Batrun: Utilizing Idle Workstations for Large-scale Computing", Summer 1996, pp. 41-48.

Brisbin, "Shopping for Internet Access", MacUser, Dec. 1994, v.10, p. 133(2).

Gilder, "The Bandwidth Tidal Wave", Forbes ASAP, Dec. 5, 1994.

N/A, "Special Report—Wonder Chips", Business Week, Jul. 4, 1994.

N/A, "Supercomputers Divide and Conquer", The Economist, Dec. 14, 1996.

N/A, "Cyber View World Widgets", Scientific American, May 1997, p. 48.

Gibbs, "Bandwidth, Unlimited", Scientific American, Jan. 1997, p. 41.

Markoff, "A New Standard to Govern PC's with Multiple Chips, Work Stations Mimicking Supercomputers", The New York Times, Oct. 28, 1997.

N/A, "Aliens on your desktop", The Economist, Apr. 18, 1998, p. 78.

Hare et al., "Master the Complexities of Network Security" *Internet Firewalls and Network Security*. Second Edition, pp. 325-350 and 516.

Fox et al., Petaops and Exaops: Supercomputing on the Web, "IEEE Internet Computing", vol. 1 No. 2 Mar.-Apr. 1997, pp. 38-46.

Dincer et al., Building a World-Wide Virtual Machine Based on Web and HPCC Technologies, "Student Technical Papers", http://www.supercomp.org/sc96/proceedings/SC96PROC/DINCER/INDEX.HTM, pp. 1-18.

Hobbs et al., A Remote Process Creation and Execution Facility Supporting Parallel Execution on Distributed Systems, "IEEE 1996", pp. 92-99.

Boku et al., The Architecture of Massively Parallel Processor CP-PACS, "IEEE 1997", pp. 31-40.

Choi et al., A Diagnostic Network for Massively Parallel Processing Systems, "IEEE 1994", pp. 348-353.

Bellovin et al., Network Firewalls, "IEEE Communications Magazine 1994", pp. 50-57.

Weiyi et al., "Java-to-Go—Itinerative Computing Using Java", Sep. 10, 1996 http://ptolemy.eecs.berkeley.edu/dgm/javatools/java-to-go/.

Sullivan et al., "A New Major SETI Project Based on Project Serendip Data and 100,000 Personal Computers". http://setiathome.ss/berkeley.edu/woody_paper.htm/.

"Ein-Chip-Firewall", Elektroniknet Top News, XP-002164257.

"Means for Implementing Optical Interconnections for Parallel Processors", IBM Technical Disclosure Bulletin, Apr. 1991, vol. 33, No. 11, pp. 56-58, XP 000110310.

Alexandrov et al., "SuperWeb: Research Issues in Java-Based Global Computing", Concurrency, vol. 9, No. 6, Jun. 1997, pp. 535-553.

Baratloo et al., "Charlotte: Metacomputing on the Web", 9th International Conference on Parallel and Distributed Computing Systems (PDCS), 1996, pp. 1-8.

Bevinakoppa et al., "Digital Image Compression on a Network of Transputers", Proc. of 5th Australian Transputer & OCCAM User Group Conference, IOS Press, Amsterdam, pp. 25-32.

Blumofe, R. et al., "Scheduling Large-Scale Parallel Computations on Networks of Workstations", Proc. of the 3rd IEEE Int'l Sump on High Performance Distributed Computing, pp. 96-105, Aug. 1994.

Fields, Scott, "Hunting for Wasted Computing Power—New Software for Computing Networks Plus Idle PC's to Work", 1993 University of Wisconsin—Madison. Internet: http://www.cs.wise.edu/condor/doc/Wiseidea.html.

(56) References Cited

OTHER PUBLICATIONS

Brecht et al., "ParaWeb: Towards World-Wide Supercomputing", Proceedings of the Seventh AcM SIGOPS European Workshop, Sep. 1996, 8 pgs.
Capello et al., "Market-Based Massively Parallel Internet Computing", Proceedings Third Working Conference on Massively Parallel Programming Models, 1998, pp. 118-129.
Celenk; M. et al., "Parallel Task Execution in LANs and Performance Analysis", Proc. of the 1995 IEEE 14th Annual Int'l Phoenix Conf. on Computers and Communications, pp. 423-429, Mar. 1995.
Chen, C. et al., "The DBC: Processing Scientific Data Over the Internet", Proc. of the 16th Int'l Conf. on Distributed Computing Systems, pp. 673-679, May 1996.
Clark, H. et al., "DAWGS—A Distributed Computer Server Utilizing Idle Workstations", Proc. of the 5th Distributed Memory Computing Conf., IEEE, pp. 732-741, Apr. 1990.
Fogg, C., "Survey of Software and Hardware VLC Architectures", SPIE, vol. 2186, Image and Video Compression (1994), pp. 29-37.
Fox et al., "Towards Web/Java based High Performance Distributed Computing—an Evolving Virtual Machine", as presented at 5th IEEE Int'l Symposium on High Performance Distributed Computing, Aug. 6-9, 1996, 86 pages.
Fox, E., "Advances in Interactive Digital Multimedia Systems", Computer, Oct. 1991, pp. 9-21.
Gemmell, et al., "Multimedia Storage Servers: a Tutorial", Computer, May 1995, pp. 40-49.
Hayes, "Computing Science: Collective Wisdom", American Scientist, Mar.-Apr. 1998, pp. 1-8.
Kim, B., "ATM Network: Goals and Challenges", Communications of the ACM, Feb. 1995, vol. 38, No. 2, pp. 39-44, 109.
Kremien, O., "Buying and Selling Computational Power Over the Network", Proc. of the 4th Int'l Conf. on Computer Communications and Networks, IEEE, pp. 616-619, Sep. 1995.
Lindley, C., "JPEG-Like Image Compression, Part 2", Dr. Dobb's Journal, Aug. 1995, pp. 62-66, 102-105.
Lindley, C., "JPEG-Like Image Compression, Part 1", Dr. Dobb's Journal, Jul. 1995, pp. 50-58, 101-102.
Morris, J. et al., "Fault Tolerant Networks of Workstations", Proc. of the 3rd Int'l. Conf. on High Performance Computing, IEEE, pp. 271-276, Dec. 1996.
Nass, R., "Hardware-software combo could simplify MPEG real-time video compression", Electronic Design, May 3, 1993, p. 36.
Nowatzyk et al., "Are Crossbars Really Dead? The Case for Optical Multiprocessor Interconnect Systems", Proceedings of the Annual Symposium on Computer Architecture, ACM, vol. 22, Jun. 1995, pp. 106-115, XP 000687800.
Ozer, "Digital Video: Shot by Shot", PC Magazine, Apr. 11, 1995, pp. 104-107, 110.
Ozer, J., "Why MPEG is Hot", PC Magazine, Apr. 11, 1995, pp. 130-131.
Plotkin, "The Digital Compression Facility—A Solution to Today's Compression Needs", 1994 IEEE, pp. 445-449.
Qiao et al., "Time-Division Optical Communications in Multiprocessor Arrays", ACM, 1991, pp. 644-653, XP 000337522.
Rincon et al., "The Changing Landscape of System-on-a-chip Design", MicroNews, Third Quarter 1999, www.chips.ibm.com/micronews/vol5_no3/rincon.html, pp. 1-10, vol. 5, No. 3.
Sachs, M. et al., "LAN and I/O Convergence: A Survey of the Issues", Computer, Dec. 1994, pp. 24-32.
Sakano, et al., "A Three-Dimensional Mesh Multiprocessor System Using Board-to-Board Free-Space Optical Interconnects: COSINE-III", IEEE, 1993, pp. 278-283, XP 000463415.
Schroeder, E., "New Offerings Buoy MPEG as Video Standard", Desktop Computing, PC Week, May 8, 1995, pp. 1 and 29.
Shen et al., "A Parallel Implementation of an MPEG1 Encoder: Faster than Real-Time", Proc. of SPIE Conf. on Digital Video Compression, San Jose, CA, Feb. 1995.
McHenry et al., "An FPGA-Based Coprocessor for ATM Firewalls", Field-Programmable Custom Computing Machines 1997, Apr. 16-18, 1997, pp. 30-39, XP-002157218.
Shiuan, J. et al., "Client-Server Based Ray-Tracer Using ASTRA: An Asynchronous RPC Mechanism", Computer Communications, vol. 19, No. 5, pp. 445-455, May 1996.
Szabo, B. et al., "Design Considerations for JPEG Video and Synchronized Audio in a Unix Workstation Environment", USENIX—Summer '91, pp. 353-368.
Vetter, R., "ATM Concepts, Architectures, and Protocols", Communications of the ACM, Feb. 1995; vol. 38, No. 2, pp. 30-38, 109.
Vetter, R. et al., "Issues and Challenges in ATM Networks", Communications of the ACM, Feb. 1995; vol. 38, No. 2, pp. 28-29.
Waldspurger et al., "Spawn: A Distributed Computational Economy", IEEE Transactions on Software Engineering, vol. 18, No. 2, Feb. 1992, pp. 103-117 XP002124500.
Yoshida, J., "MPEG-2 Encoders Make Show of Force at NAB", Electronic Engineering Times, Apr. 10, 1995.
Yu, Y. et al., "Software Implementation of MPEG-II Video Encoding Using Socket Programming in LAN", SPIE vol. 2187, pp. 229-240, 1994.
Waltz et al., "Make 'em pay: Billing Net Usage", MacWeek, vol. 6 (No. 27), p. 24 (2) (Dialog full text), (Jul. 27, 1992).
"The Economics of Network Billing: Network Billing and Monitoring Systems can Improve Efficiency and Cut Costs"; IBM System User, vol. 14 (No. 11), p. 53 (1) (Dialog Fulltext), (Nov. 1993).
"Let Your Computer Make Money While You Sleep", Newsbytes, p. 1 (Dialog Fulltext), (Aug. 16, 1996).
Regenold et al., "A Single-Chip Multiprocessor DSP Solution for Communication Applications", ASIC Conference and Exhibit 1994, pp. 437-440.
Geppert, L. Solid State [Trend/Development], IEEE Spectrum, v. 33, iss. 1, 1996, pp. 51-55.
Li; Yao, "Free-space Optical Bus-based WDMA Interconnects for Parallel Computation", LEOS '92 Conference Proceedings, Lasers and Electron-Optics Society Annual Meeting, p. 588-589, Nov. 16-19, 1992.
Dickinson et al., "An Integrated Free Space Optical Bus", 1989 IEEE International Conference on Computer Design, VLSI in Computers and Processors, p. 62-65, Oct. 2-4, 1989.
Natarajan et al., "Bi-Directional Optical Backplane Bus for General Purpose Multi-Processor", Journal of Lightwave Technology, vol. 13; No. 6, p. 1031-1040, Jun. 6, 1995.
Zhao et al., "General Purpose Bidirectional Optical Backplane: High Performance Bus for Multiprocessor Systems", Massively Parallel Processing Using Optical Interconnections, 2nd International Conference, p. 188-195, Oct. 23-24, 1995.
Wu et al., "Microprocessor Control Signal Transmission Through Optical Fiber", Conference Record of 1992, IEEE Industry Applications Society Annual Meeting, p. 1747-1750, Oct. 4-9, 1992.
Fox et al., "Towards Web/Java based High Performance Distributed Computing—an Evolving Virtual Machine", www.npac.syr.edu/projects/webspace/doc/hpdc5/paper, Jun. 10, 1996, 11 pages.
None, "PC Vision: Intel unveils plans to bring PCs to Vehicles"; EDGE: Work-Group Computing Report, EDGE Publishing, p. 1-2 (Oct. 28, 1996).
The American Heritage College Dictionary 4th Ed.—definition of "firewall".
White, "Covert Distributed Processing with Computer Viruses", Advances in Cryptology, Crypto 89, Springer LNCS, v. 435, pp. 616-619.
Foster et al., "The Grid: Blueprint for a New Computing Infrastructure", Morgan Kaufman Publishers, Inc., 1998.
Hwang et al., "Scalable Parallel Computing", WCB McGraw-Hill, 1998.
Wilkinson, et al., "Parallel Programming", Prentice Hall, 1998.
Patterson et al., "Computer Architecture: A Quantitative Approach" (2nd Edition), Morgan Kaufmann Publishers, Inc., 1996.
Culler et al., "Parallel Computer Architecture", Morgan Kaufmann Publishers, Inc., 1998.
Hennessy et al., "Computer Organization and Design", Morgan Kauffmann Publishers, Inc., 1998.
Slater, "The Microprocessor Today", IEEE Micro 1996, pp. 32-44.
Steinert-Threlkeld; "New Breed of Chip TI develops a super circuit"; The Sun Baltimore; May 4, 1992.

(56) References Cited

OTHER PUBLICATIONS

Dallas Morning News; "LSI holds big plans for tiny chips Versatility of 'system on a chip' creates niche in microelectronics;" Mar. 4, 1996.
Mokhoff; "System-on-a-chip comes to wireless arena;" Electronic Engineering Times; Feb. 12, 1996.
Cindi; "System on a Chip' stars at ISSCC;" Electronic News; Feb. 19, 1996.
Ang; "System-on-a-chip to define next-generation set-top box"; Electronic Engineering Times; Dec. 15, 1995.
Marc; "New family of microprocessor cores from LSI Logic extends customers' system-on-a-chip design capability" Nov. 7, 1994.
Wall Street Journal; "Technology Brief—Advance Micro Devices Inc.: Company unveils Microchip for Hand-Held Computers"; Oct. 18, 1993.
Gelsinger, Patrick et al. "Microprocessors circa 2000," IEEE Spectrum, Oct. 1989 pp. 43-47.
Yu, Albert. "The Future of Microprocessors," IEEE Micro, Dec. 1996, pp. 46-53.
McWilliams. "Dell to Phase Out Computers Using Intel's Itanium," The Wall Street Journal, Online, Sep. 15, 2005.
David Pescovitz, "Power of the PC", Scientific American, pp. 27-28 (Apr. 2000).
Stephen H. Wildstrom, "The Problem with Firewalls", Business Week, pp. 25 (Mar. 20, 2000).
J. McH., "Build Your Own Supercomputer", Forbes, pp. 228 (Nov. 15, 1999).
Office Action issued in co-pending U.S. Appl. No. 10/802,049 dated Sep. 17, 2007.
Office Action issued in related U.S. Appl. No. 09/085,755 mailed Dec. 12, 2007.
Office Action issued in related U.S. Appl. No. 09/884,041 mailed Dec. 12, 2007.
Office Action issued in related U.S. Appl. No. 09/935,779 mailed Feb. 19, 2008.
Notice of Allowance issued in U.S. Appl. No. 09/884,041 mailed May 22 2008.
Notice of Allowance issued in U.S. Appl. No. 09/085,755 mailed Jun. 25, 2008.
Final Office Action issued in U.S. Appl. No. 10/802,049 mailed Jul. 3, 2008.
Notice of Allowance issued in U.S. Appl. No. 09/935,779 mailed Jul. 18, 2008.
Wilkinson, Barry et al., "Parallel Programming: Techniques and Applications Using Networked Workstations and Parallel Computers", Chapter 4, Prentice-Hall, Inc., 1999.
Baker, Lou et al., "Parallel Programming", Chapter 4, McGraw Hill Companies, Inc., 1996.
Kayssi, A.; Hark, L.; Ferzli, R.; Fawaz, M; "FPGA-based Internet Protocol Firewall Chip"; Electronics, Circuits and Systems, 2000. ICECS 2000. The 7th IEEE International Conference on vol. 1, Dec. 17-20, 2000 pp. 316-319 vol. 1,[retrieved from IEEE database Jun. 9, 2008].
Office Action issued in U.S. Appl. No. 10/663,911 mailed Sep. 26, 2008.
Notice of Allowance issued in U.S. Appl. No. 09/884,041 mailed Oct. 9, 2008.
Notice of Allowance issued in U.S. Appl. No. 09/935,779 mailed Jan. 21, 2009.
English language abstract of EP 0 647 052, published Apr. 5, 1995.
Newton's Telecom Dictionary, "Mobile IP", p. 459, Mar. 1998.
Holographic Quantum Computer, http://www.unitelnw.com/holo1/index (May 1999).
Jonathan Fahey, "Screen Grab", Forbes, pp. 52-53, Mar. 5, 2001.
Ronald Grover et al., "TV Guy", Business Week, pp. 66-76, Mar. 12, 2001.
"Distributed Computing", Red Herring, No. 87, pp. 166-202, Dec. 18, 2000.
Om Malik, "Distributed Computing Redefines Computer Networks, Underpinning Innovation, Company Formation, and Investments", Red Herring, No. 86, pp. 95-96 and 105, Dec. 4, 2000.
Alan Zeichick, "P2P Nework Expalined", Red Herring, No. 86, pp. 204 and 206, Dec. 4, 2000.
"Napster is Clouding Grove's Crystal Ball"; Fortune, pp. 271-272, May 29, 2000.
Notice of Allowance issued in U.S. Appl. No. 09/884,041 mailed Mar. 9, 2009.
Notice of Allowance issued in U.S. Appl. No. 09/085,755 mailed Apr. 8, 2009.
Office Action issued in U.S. Appl. No. 10/663,911, mailed Jun. 26, 2009.
Gordon Force, Sr., "Portable Data Encryption Approaches", WESTCON/'95, Conference Record: Microelectronics Communications Technology Producing Quality Production Mobile and Portable Power emerging Technologies, Nov. 7-9, 1995, pp. 413-419.
A.D. Romig, Jr., "High Performance Microsystem Packaging: A Perspective", Microelectron Reliab., vol. 37, No. 10/11, pp. 1771-1781 (1997).
Office Action issued in U.S. Appl. No. 10/802,049, mailed Jul. 1, 2009.
Office Action issued in U.S. Appl. No. 11/329,423, mailed Sep. 18, 2009.
Office Action issued in U.S. Appl. No. 10/663,911, mailed Mar. 15, 2010.
Notice of Allowance issued in U.S. Appl. No. 10/802,049, mailed Apr. 2, 2010.
Notice of Allowance issued in U.S. Appl. No. 10/663,911, mailed Jun. 7, 2010.
Office Action issued in U.S. Appl. No. 11/196,527, mailed May 24, 2010.
Office Action issued in U.S. Appl. No. 11/338,887, mailed May 21, 2010.
Office Action issued in U.S. Appl. No. 11/329,423, mailed Jun. 21, 2010.
Notice of Allowance issued in U.S. Appl. No. 11/196,527, mailed Oct. 29, 2010.
Notice of Allowance issued in U.S. Appl. No. 11/338,887, mailed Nov. 2, 2010.
Office Action issued in U.S. Appl. No. 12/499,555, mailed Nov. 24, 2010.
Office Action issued in U.S. Appl. No. 12/364,745, mailed Nov. 23, 2010.
O. M. Woodward et al., "The Omniguide Antenna; An Omnidirectional Waveguide Array for UHF-TV Broadcasts", IRE International Convention Records, pp. 37-39, Mar. 1955.
File History of U.S. Appl. No. 11/196,527.
File History of U.S. Appl. No. 11/338,887.
File History of U.S. Appl. No. 12/364,745.
File History of U.S. Appl. No. 11/329,423.
Office Action issued in U.S. Appl. No. 12/822,928, mailed Sep. 12, 2011.
Notice of Allowance issued in U.S. Appl. No. 12/164,661, mailed Oct. 25, 2011.
File History of U.S. Appl. No. 12/499,555.
File History of U.S. Appl. No. 13/495,867.
File History of U.S Appl. No. 10/684,657.
File History of U.S Appl. No. 08/980,058.
File History of U.S Appl. No. 09/085,755.
File History of U.S Appl. No. 09/213,875.
File History of U.S Appl. No. 09/315,026.
File History of U.S Appl. No. 09/320,660.
File History of U.S Appl. No. 09/571,558.
File History of U.S Appl. No. 09/669,730.
File History of U.S Appl. No. 09/884,041.
File History of U.S Appl. No. 09/935,779.
File History of U.S Appl. No. 10/663,911.
File History of U.S Appl. No. 10/802,049.
File History of U.S Appl. No. 11/329,423.
File History of U.S Appl. No. 13/016,149.
File History of U.S Appl. No. 13/018,089.
File History of U.S Appl. No. 13/240,842.
File History of U.S Appl. No. 13/599,484.
File History of U.S Appl. No. 12/292,769.
File History of U.S Appl. No. 12/292,553.

(56) References Cited

OTHER PUBLICATIONS

File History of U.S Appl. No. 13/426,133.
File History of U.S Appl. No. 13/398,403.
File History of U.S Appl. No. 13/555,750.
File History of U.S Appl. No. 13/404,888.
File History of U.S Appl. No. 13/180,164.
Fengling Shao et al., "a new secure architecture of network computer based on single CPU and Dual Bus" Fifth IEEE International Symposium on Embedded Computing, pp. 309-314 (2008).
Tiedong Wang et al., "A Hardware implement of Bus Bridge Based on Single CPU and Dual Bus", 2008 International Symposium on Computer Science and Computational Technology, pp. 17-20 (2008).
Famatech "Radmin V3.0, User Manuel", Jun. 3, 2007 (203 pages).
Connect One, iChip CO2064/CO2128/CO2144, 2007 (203 2011 (64 pages).
Complete file history for U.S. Appl. No. 13/014,201.
Complete file history for U.S. Appl. No. 13/016,527.
Complete file history for U.S. Appl. No. 13/328,697.
File History of U.S. Appl. No. 12/164,661.
File History of U.S. Appl. No. 12/822,928.
File History of U.S. Appl. No. 13/016,149.
File History of U.S. Appl. No. 13/018,089.
File History of U.S. Appl. No. 13/283,274.
File History of U.S. Appl. No. 13/594,614.
File History of U.S. Appl. No. 13/599,484.
File History of U.S. Appl. No. 13/180,164.
File History of U.S. Appl. No. 13/240,842.
File History of U.S. Appl. No. 13/240,842, electronically for Apr. 2, 2013 to Jul. 2, 2013.
FIle History of U.S. Appl. No. 13/594,614, electronically captured from May 16, 2013 to Jul. 2, 2013.
File History of U.S. Appl. No. 13/016,149, electronically captured for May 1, 2013 to Aug. 1, 2013.
File History of U.S. Appl. No. 13/018,089, electronically captured for May 1, 2013 to Aug. 1, 2013.
File History of U.S. Appl. No. 13/599,484, electronically captured for May 1, 2013 to Aug. 1, 2013.
File History of U.S. Appl. No. 13/180,164, electronically captured for Mar. 27, 2013 to May 16, 2013.
FIle History of U.S. Appl. No. 13/495,867, electronically captured for Feb. 16, 2013 to May 16, 2013.
File History of U.S. Appl. No. 13/594,614, electronically captured for Feb. 16, 2013 to May 16, 2013.

\* cited by examiner

FIG. 10"O"

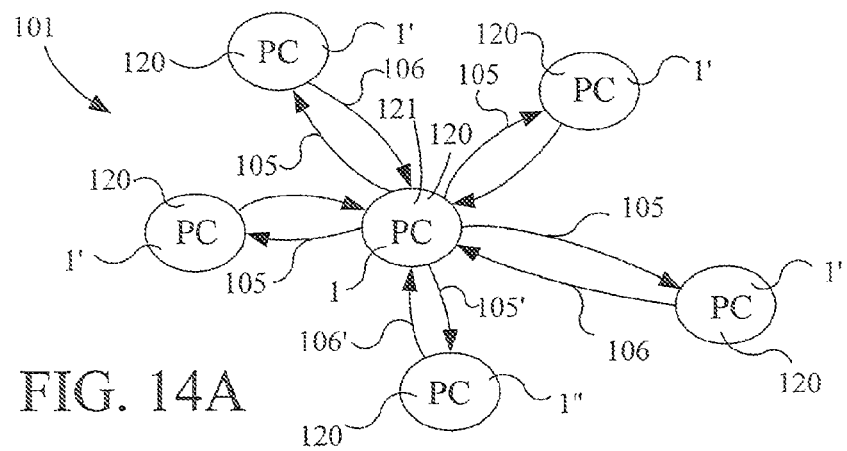
FIG. 14A
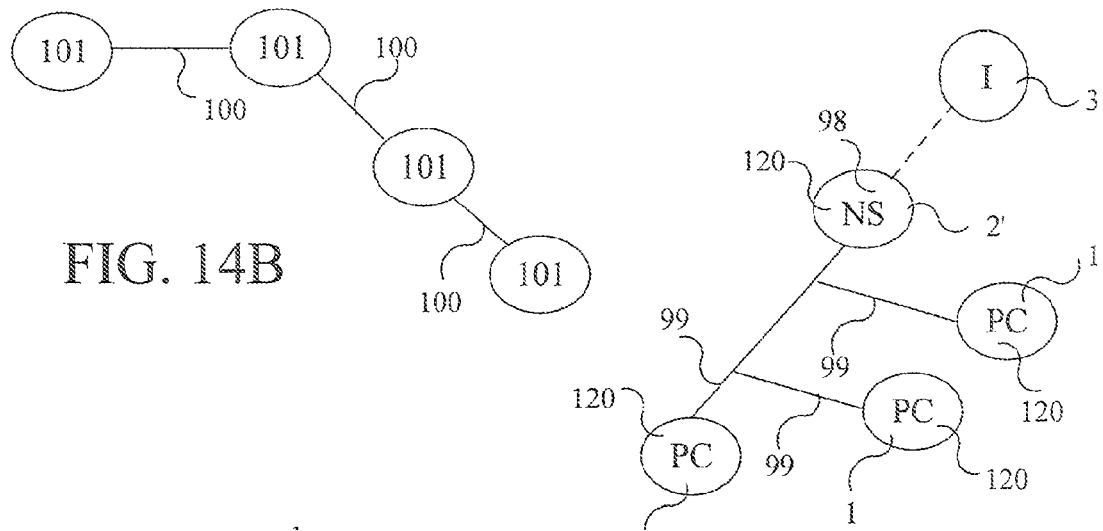
FIG. 14B
FIG. 14D
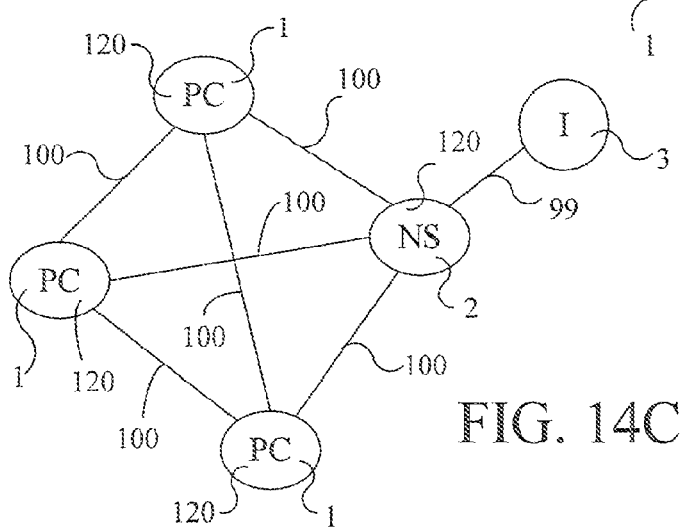
FIG. 14C
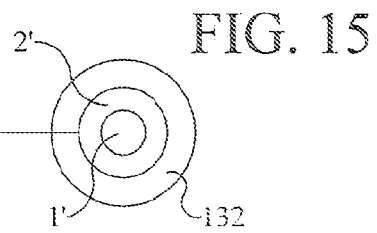
FIG. 15

COMPUTERS AND MICROCHIPS WITH A SIDE PROTECTED BY AN INTERNAL HARDWARE FIREWALL AND AN UNPROTECTED SIDE CONNECTED TO A NETWORK

This application is a continuation of U.S. patent application Ser. No. 10/663,911, filed Sep. 17, 2003, which is a continuation of U.S. patent application Ser. No. 09/213,875, filed Dec. 17, 1998, which receives the benefit of priority from provisional application No. 60/068,366, filed on Dec. 19, 1997, and is a continuation-in-part of U.S. patent application Ser. No. 08/980,058, filed Nov. 26, 1997, which receives the benefit of priority of provisional application No. 60/066,415, filed Nov. 24, 1997, provisional application No. 60/066,313, filed Nov. 21, 1997, provisional application No. 60/033,871, filed Dec. 20, 1996, provisional application No. 60/032,207 filed Dec. 2, 1996, and provisional application No. 60/031,855, filed Nov. 29, 1996. U.S. patent application Ser. No. 09/213,875 is also a continuation-in-part of PCT application PCT/US97/21812, filed Nov. 28, 1997 and designating the United States. PCT/US97/21812 receives the benefit of priority of provisional application No. 60/066,415, filed Nov. 24, 1997, provisional application No. 60/066,313, filed Nov. 21, 1997, provisional application No. 60/033,871, filed Dec. 20, 1996, provisional application No. 60/032,207 filed Dec. 2, 1996, and provisional application No. 60/031, 855, filed Nov. 29, 1996. PCT/US97/21812 is a continuation-in-part of U.S. patent application Ser. No. 08/980,058, whose priority is discussed above.

BACKGROUND OF THE INVENTION

This invention generally relates to one or more computer networks having computers like personal computers or network computers such as servers with microprocessors preferably linked by broadband transmission means and having hardware, software, firmware, and other means such that at least two parallel processing operations occur that involve at least two sets of computers in the network or in networks connected together, a form of metacomputing. More particularly, this invention relates to one or more large networks composed of smaller networks and large numbers of computers connected, like the Internet, wherein more than one separate parallel or massively parallel processing operation involving more than one different set of computers occurs simultaneously. Even more particularly, this invention relates to one or more such networks wherein more than one (or a very large number of) parallel or massively parallel microprocessing processing operations occur separately or in an interrelated fashion; and wherein ongoing network processing linkages can be established between virtually any microprocessors of separate computers connected to the network.

Still more particularly, this invention relates generally to a network structure or architecture that enables the shared used of network microprocessors for parallel processing, including massive parallel processing, and other shared processing such as multitasking, wherein personal computer owners provide microprocessor processing power to a network, preferably for parallel or massively parallel processing or multitasking, in exchange for network linkage to other personal and other computers supplied by network providers such as Internet Service Providers (ISP's), including linkage to other microprocessors for parallel or other processing such as multitasking. The financial basis of the shared use between owners and providers being be whatever terms to which the parties agree, subject to governing laws, regulations, or rules, including payment from either party to the other based on periodic measurement of net use or provision of processing power or preferably involving no payment, with the network system (software, hardware, etc) providing an essentially equivalent usage of computing resources by both users and providers (since any network computer operated by either entity can potentially be both a user and provider of computing resources alternately (or even simultaneously, assuming multitasking), with potentially an override option by a user (exercised on the basis, for example, of user profile or user's credit line or through relatively instant payment).

Finally, this invention relates to a network system architecture including hardware and software that provides use of the Internet or its future equivalents or successors (and most other networks) without cost to most users of personal computers or most other computers, while also providing those users (and all other users, including of supercomputers) with computer processing performance that can at least double every 18 months through metacomputing means. This metacomputing performance increase provided by the new MetaInternet (or Metanet for short) is in addition to all other performance increases, such as those already anticipated by Moore's Law.

By way of background, the computer industry has been governed over the last 30 years by Moore's Law, which holds that the circuitry of computer chips has been shrunk substantially each year, yielding a new generation of chips every 18 months with twice as many transistors, so that microprocessor computing power is effectively doubled every year and a half.

The long term trend in computer chip miniaturization is projected to continue unabated over the next few decades. For example, slightly more than a decade ago a 16 kilobit DRAM memory chip (storing 16,000 data bits) was typical; the standard in 1996 was the 16 megabit chip (16,000,000 data bits), which was introduced in 1993; and industry projections are for 16 gigabit memory chips (16,000,000,000 data bits) to be introduced in 2008 and 64 gigabit chips in 2011, with 16 terabit chips (16,000,000,000,000 data bits) conceivable by the mid-to-late 2020's. This is a thousand-fold increase regularly every fifteen years. Hard drive speed and capacity are also growing at a spectacular rate.

Similarly regular and enormous improvements are anticipated to continue in microprocessor computing speeds, whether measured in simple clock speed or MIPS (millions of instructions for second) or numbers of transistors per chip. For example, performance has improved by four or five times every three years since Intel launched its X86 family of microprocessors used in the currently dominant "Wintel" standard personal computers. The initial Intel Pentium Pro microprocessor was introduced in 1995 and is a thousand times faster than the first IBM standard PC microprocessor, the Intel 8088, which was introduced in 1979. By 1996 the fastest of microprocessors, like Digital Equipment Corp.'s Alpha chip, is faster than the processor in the original Cray Y-MP supercomputer.

Both microprocessors and software (and firmware and other components) are also evolving from 8 bit and 16 bit systems into 32 bit systems that are becoming the standard today, with some 64 bit systems like the DEC Alpha already introduced and more coming, with future increases to 128 bit also likely.

A second major development trend in the past decade or so has been the rise of parallel processing, a computer architecture utilizing more than one CPU microprocessor (often many more, even thousands of relatively simple microprocessors, for massively parallel processing) linked together into a single computer with new operating systems having modifications that allow such an approach. The field of supercomputing has been taken over by this approach, including designs utilizing many identical standard personal computer microprocessors.

Hardware, firmware, software and other components specific to parallel processing are in a relatively early stage of development compared to that for single processor computing, and therefore much further design and development is expected in the future to better maximize the computing capacity made possible by parallel processing. One likely improvement is much more effective system architecture for parallel processing that does not rely on the multiple microprocessors having to share memory, thereby allowing more independent operation of those microprocessors, each with their own discrete memory, like current personal computers, workstations and most other computer systems architecture; for unconstrained operation, each individual microprocessor must have rapid access to sufficient memory.

Several models of personal computers are now available with more than one microprocessor. It seems inevitable that in the future personal computers, broadly defined to include versions not currently in use, will also employ parallel computing utilizing multiple microprocessors or massively parallel computing with very large numbers of microprocessors. Future designs, such Intel's Merced chip, are expected to have a significant number of parallel processors on a single microprocessor chip.

A form of parallel processing is also being employed within microprocessor design itself. The generation in 1996 of microprocessors such at the Intel Pentium have more than one data path within the microprocessor in which data can be processed, with two to three paths being typical.

The third major development trend is the increasing size of bandwidth, which is a measure of communications power between computers connected by a network. Before now, the local area networks and telephone lines typically linking computers including personal computers have operated at speeds much lower than the processing speeds of a personal computer. For example, a typical Intel Pentium operates at 100 MIPS (millions of instructions per second), whereas a typical Ethernet connecting the PC's is 100 times slower at 10 megabits per second (Mbps) and telephone lines are very much slower, the highest typical speed now being about 28.8 kilobits per second.

Now, however, the situation is expected to change dramatically, with bandwidth being anticipated to expand from 5 to 100 times as fast as the rise of microprocessor speeds, due to the use of coaxial cable, wireless, and fiber optic cable. Telecommunication providers are now making available fiber connections supporting bandwidth of 40 gigabits per second.

Technical improvements are expected in the near term which will make it possible to carry over 2 gigahertz (billions of cycles per second) on each of 700 wavelength stream, adding up to more than 1,700 gigahertz on every single fiber thread. Experts believe that the bandwidth of optical fiber has been utilized one million times less fully than the bandwidth of coaxial or twisted pair copper lines. Within a decade, 10,000 wavelength streams per fiber are expected and 20 wavelengths on a single fiber is already commercially available.

Other network connection developments such as asynchronous transfer mode (ATM) and digital signal processors, which are improving their price/performance tenfold every two years, are also supporting the rapid increase in bandwidth. The increase in bandwidth reduces the need for switching and switching speed will be greatly enhanced when practical optical switches are introduced in the fairly near future, potentially reducing costs substantially.

The result of this huge bandwidth increase will be extraordinary: within just a few years when sufficient network infrastructure is in place, it will be technically possible to connect virtually any computer to a network at a speed that equals or exceeds the computer's own internal bus speed, even as that bus speed itself is increasing significantly. The bus of a computer is its internal network connecting its components such as microprocessor, random access memory (RAM), harddrive, modem, floppy drive, and CD-ROM; for recent personal computers it has been only about 40 megabits per second, but is now up to a gigabit per second on Intel's Pentium PCI bus.

Despite these tremendous improvements anticipated in the future, the unfortunate present reality is that a typical personal computer (PC) is already so fast that its microprocessor is essentially idle during most of the time the PC is in actual use and that operating time itself is but a small fraction of those days the PC is even in any use at all. The reality is that nearly all PC's are essentially idle during roughly all of their useful life. A realistic estimate is that its microprocessor is in an idle state 99.9% of the time (disregarding current unnecessary microprocessor busywork like executing screen saver programs, which have been made essentially obsolete by power-saving CRT monitor technology, which is now standard in the PC industry).

Given the fact that the reliability of PC's is so exceptionally high now, with the mean time to failure of all components typically several hundred thousand hours or more, the huge idle time of PC's represents a total loss; given the high capital and operating costs of PC's, the economic loss is very high. PC idle time does not in effect store a PC, saving it for future use, since the principle limiting factor to continued use of today's PC's is obsolescence, not equipment failure from use.

Moreover; there is growing concern that Moore's Law, which as noted above holds that the constant miniaturization of circuits results in a doubling of computing power every 18 months, cannot continue to hold true much longer. Indeed, Moore's Law may now be nearing its limits for silicon-based devices, perhaps by as early as 2004, and no new technologies have yet emerged that currently seem with reasonable certainty to have the potential for development to a practical level by then.

SUMMARY OF THE INVENTION

However, the confluence of all three of the established major trends summarized above—supercomputer-like personal computers, the spread of parallel processing using personal computer microprocessors (particularly massively parallel processing), and the enormous increase in network communications bandwidth—have made possible in the near future a surprising solution to the hugely excessive idleness problem of personal computers (and to the problematic possible end of Moore's Law), with very high potential economic savings.

The solution is use those mostly idle PC's (or their equivalents or successors) to build a parallel or massively parallel processing computer utilizing a very large network like the Internet or, more specifically, like the World Wide Web (WWW), or their equivalents or eventual successors like the MetaInternet (and including Internet II, which is under development now and which will utilize much broader bandwidth and will coexist with the Internet, the structure of which is in ever constant hardware and software upgrade) with broad bandwidth connections. The prime characteristic of the Internet is of course the very large number of computers of all sorts already linked to it, with the future potential for effectively universal connection; it is a network of networks of computers that provides nearly unrestricted access (other than cost) worldwide. The rapidly growing infrastructure of very broad bandwidth of network communications can be used to link personal computers externally in a manner equivalent to the internal buses of the personal computers, so that no processing constraint is be imposed on linked personal computers by data input or output, or throughput; the speed of the microprocessor itself can be the only processing constraint of the system.

This makes external parallel processing possible, including massively parallel processing, in a manner paralleling more conventional internal parallel processing.

Optimally, the World Wide Web (or its equivalents or successors) can be transformed into a huge virtual massively parallel processing computer or computers, with potential through its established hyperlinks connections to operate in a manner at least somewhat like a neural network or neural networks, since the speed of transmission in the broadband linkages is so great that any linkage between two microprocessors is virtually equivalent to direct, physically close connections between those microprocessors.

With further development, digital signal processor-type microprocessors or even analogue microprocessors may be optimal for this approach. Networks with WWW-type hyperlinks incorporating digital signal processor-type microprocessor (or successors or equivalents) could operate separately from networks of conventional microprocessors (or successors or equivalents) or with one or more connections between such differing networks or with relatively complete integration between such differing networks. Simultaneous operation across the same network connection structure should be possible.

Such broad bandwidth networks of computers enable every PC to be fully utilized or nearly so. Because of the extraordinary extent to which existing PC's are currently idle, at optimal performance this new system can potentially result in a thousand-fold increase in computer power available to each and every PC user (and any other user); and, on demand, almost any desired level of increased power, limited mostly by the increased cost, which however is relatively far less than possible from any other conceivable computer network configuration. This revolutionary increase is on top of the extremely rapid, but evolutionary increases already occurring in the computer/network industry discussed above.

The metacomputing hardware and software means of the MetaInternet provides performance increases that can likely at least double every eighteen months based on the doubling of personal computers shared in a typical parallel processing operation by a standard PC user, starting first with at least 2 PC's, then about 4, about 8, about 16, about 32, about 64, about 128, about 256, and about 512, for example. After about fifteen years, for example, it is anticipated that each standard PC user will likely be able to use about 1024 personal computers for parallel processing or any other shared computing use, while generally using the Internet or its successors like the MetaInternet for free. At the other end of the performance spectrum, supercomputers can experience a similar performance increase generally, but ultimately the performance increase is limited primarily by cost of adding temporary network linkages to available PC's, so there is definite potential for a quantum leap in supercomputer performance.

Network computer systems as described above offer almost limitless flexibility due to the abundant supply of heretofore idle connected microprocessors. This advantage allows "tightly coupled" computing problems (which normally are difficult to process in parallel) to be solved without knowing in advance (as is now necessary in relatively massively parallel processing) how many processors are available, what they are and their connection characteristics. A minimum number of equivalent processors (with equivalent other specs) can be easily found nearby in a massive network like the Internet and assigned within the network from those multitudes available nearby. Moreover, the number of microprocessors used can be almost completely flexible, depending on the complexity of the problem, and limited only by cost. The current problem of time delay can be solved largely by the widespread introduction of broad bandwidth connections between computers processing in parallel.

BRIEF DESCRIPTION OF THE DRAWINGS

FIG. 14A is a simplified diagram of a section of a computer network, such as the Internet, showing an embodiment of a transponder means whereby a PC can identify one or more of the closest available PC's in a network cluster to designate for shared processing by wireless means. FIG. 14B shows clusters connected wirelessly; FIG. 14C shows a wireless cluster with transponders and with a network wired connection to Internet; FIG. 14D shows a network client/server wired system with transponders.

FIG. 15 is a simplified diagram of a section of a computer network, such as the Internet, showing an embodiment of a routing means whereby a PC request for shared processing can be routed within a network using preferably broad bandwidth connection means to another area in a network with one or more idle PC's available.

DETAILED DESCRIPTION OF THE PREFERRED EMBODIMENTS

Figure 1:
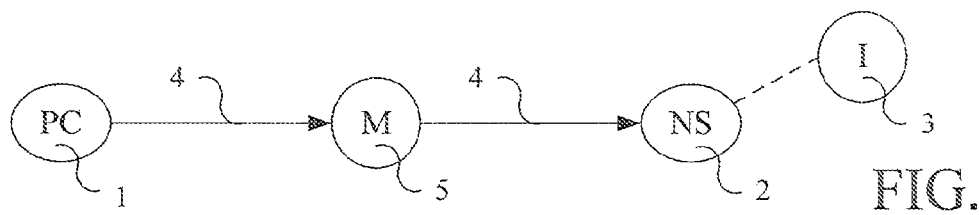
FIG. 1 is a simplified diagram of a section of a computer network, such as the Internet, showing an embodiment of a meter means which measures flow of computing during a shared operation such as parallel processing between a typical PC user and a network provider.

The new network computer utilizes PC's as providers of computing power to the network, not just users of network services. These connections between network and personal computer are enabled by a new form of computer/network financial structure that is rooted on the fact that economic resources being provided the network by PC owners (or leaser) are similar in value to those being provided by the network provider providing connectivity.

Unlike existing one way functional relationships between network providers such as internet service providers (often currently utilizing telecommunications networks for connectivity) and PC users, wherein the network provider provides access to a network like the Internet for a fee (much like cable TV services), this new relationship recognizes that the PC user is also providing the network access to the user's PC for parallel computing use, which has a similar value. The PC thus both provides and uses services on the network; alternatively or potentially even virtually simultaneously, in a multitasking mode.

This new network operates with a structural relationship that is roughly like that which presently exists between an electrical power utility and a small independent power generator connected to the utility, wherein electrical power can flow in either direction depending on the operating decisions of both parties and at any particular point in time each party is in either a debt or credit position relative to the other based on the net direction of that flow for a given period, and is billed accordingly. In the increasingly deregulated electrical power industry, electrical power (both its creation and transmission) is becoming a commodity bought and sold in a competitive marketplace that crosses traditional borders. With the structural relationship proposed here for the new network, parallel free market structures can develop over time in a new computer power industry dominated by networks of personal computers in all their forms providing shared processing.

For this new network and its structural relationships, a network provider is defined in the broadest possible way as any entity (corporation or other business, government, not-for-profit, cooperative, consortium, committee, association, community, or other organization or individual) that provides personal computer users (very broadly defined below) with initial and continuing connection hardware and/or software and/or firmware and/or other components and/or services to any network, such as the Internet and Internet II or WWW or their present or future equivalents, coexistors or successors, like the MetaInternet, including any of the current types of Internet access providers (ISP's) including telecommunication companies, television cable or broadcast companies, electrical power companies, satellite communications companies, or their present or future equivalents, coexistors or successors. The connection means used in the networks of the network providers, including between personal computers or equivalents or successors, is preferably very broad bandwidth, by such means as fiber optic cable or wireless for example, but not excluding any other means, including television coaxial cable and telephone twisted pair, as well as associated gateways, bridges, routers, and switches with all associated hardware and/or software and/or firmware and/or other components and their present or future equivalents or successors. The computers used by the providers include any computers, including mainframes, minicomputers, servers, and personal computers, and associated their associated hardware and/or software and/or firmware and/or other components, and their present or future equivalents or successors.

Other levels of network control beyond the network provider can also exist to control any aspect of the network structure and function, any one of which levels may or may not control and interact directly with the PC user. For example, at least one level of network control like the World Wide Web Consortium (W3C) or Internet Society (ISOC) or other ad hoc industry consortia can establish and ensure compliance with any prescribed network standards and/or protocols and/or industry standard agreements for any hardware and/or software and/or firmware and/or other component connected to the network. Under the consensus control of these consortia/societies, other levels of network control can deal with administration and operation of the network. These other levels of network control can potentially be constituted by any network entity, including those defined immediately above for network providers.

The principal defining characteristic of the network herein described being communication connections (including hardware and/or software and/or firmware and/or other component) of any form, including electromagnetic (such as light and radio or microwaves) and electrochemical (and not excluding biochemical or biological), between PC users, optimally connecting (either directly or indirectly) the largest number of users possible, like the Internet (and Internet II) and WWW and equivalents and successors, like the MetaInternet. Multiple levels of such networks can coexist with different technical capabilities, like Internet and Internet II, but would certainly have interconnection and therefore would certainly communicate freely between levels, for such standard network functions as electronic mail, for example.

And a personal computer (PC) user is defined in the broadest possible way as any individual or other entity using a personal computer, which is defined as any computer, digital or analog or neural, particularly including microprocessor-based personal computers having one or more microprocessors (each including one or more parallel processors) in their general current form (hardware and/or software and/or firmware and/or any other component) and their present and future equivalents or successors, such as workstations, network computers, handheld personal digital assistants, personal communicators such as telephones and pagers, wearable computers, digital signal processors, neural-based computers (including PC's), entertainment devices such as televisions, video tape recorders, videocams, compact or digital video disk (CD or DVD) player/recorders, radios and cameras, other household electronic devices, business electronic devices such as printers, copiers, fax machines, automobile or other transportation equipment devices, and other current or successor devices incorporating one or more microprocessors (or functional or structural equivalents), especially those used directly by individuals, utilizing one or more microprocessors, made of inorganic compounds such as silicon and/or other inorganic or organic compounds; current and future forms of mainframe computers, minicomputers, microcomputers, and even supercomputers are also be included. Such personal computers as defined above have owners or Teasers, which may or may not be the same as the computer users. Continuous connection of computers to the network, such as the Internet, WWW, or equivalents or successors, is preferred, but clearly not required, since connection can also be made at the initiation of a shared processing operation.

Parallel processing is defined as one form of shared processing involving two or more microprocessors used in solving the same computational problem or other task. Massively parallel microprocessor processing involves large numbers of microprocessors. In today's technology, massive parallel processing can probably be considered to be about 64 microprocessors (referred to in this context as nodes) and over 7,000 nodes have been successfully tested in an Intel supercomputer design using PC microprocessors (Pentium Pros). It is anticipated that continued software improvements will make possible effective use of a much larger number of nodes, very possibly limited only by the number of microprocessors available for use on a given network, even an extraordinarily large one like the Internet or its equivalents and/or successors, like the MetaInternet.

Broadband wavelength or broad bandwidth network transmission is defined here to mean a transmission speed (usually measured in bits per second) that is at least high enough (or roughly at least equivalent to the internal clock speed of the microprocessor or microprocessors times the number of microprocessor channels equaling instructions per second or operations per second or calculations per second) so that the processing input and output of the microprocessor is substantially unrestricted, particularly including at peak processing levels, by the bandwidth of the network connections between microprocessors that are performing some form of parallel processing, particularly including massive parallel processing. Since this definition is dependent on microprocessor speed, it increases as microprocessor speeds increase. A rough example might be a 1996 era 100 MIPS (millions instructions per second) microprocessor, for which a broad bandwidth connection is greater than 100 megabits per second (Mbps); this is a rough approximation. However, a preferred connection means referenced above is fiber optic cable, which in 1996 already provided multiple gigabit bandwidth on single fiber thread and will improve significantly in the future, so the use of fiber optic cable virtually assures broad bandwidth for data transmission that is far greater than microprocessor speed to provide data to be transmitted. The connection means to provide broad bandwidth transmission can be either wired or wireless, with wireless generally preferred for mobile personal computers (or equivalents or successors) and as otherwise indicated below. Wireless connection bandwidth is also increasing rapidly and can be considered to offer essentially the same benefit as fiber optic cable: data transmission speed that far exceeds data processing speed.

The financial basis of the shared use between owners/Teasers and providers is whatever terms to which the parties agree, subject to governing laws, regulations, or rules, including payment from either party to the other based on periodic measurement of net use or provision of processing power.

In one embodiment, as shown in FIG. 1, in order for this network structure to function effectively, there is a meter device 5 (comprised of hardware and/or software and/or firmware and/or other component) to measure the flow of computing power between PC 1 user and network 2 provider, which might provide connection to the Internet and/or World Wide Web and/or Internet II and/or any present or future equivalent or successor 3, like the MetaInternet. In one embodiment, the PC user should be measured by some net rating of the processing power being made available to the network, such as net score on one or more standard tests measuring speed or other performance characteristics of the overall system speed, such as PC Magazine's benchmark test program, ZD Winstone (potentially including hardware and/or software and/or firmware and/or other component testing) or specific individual scores for particularly important components like the microprocessor (such as MIPS or millions of instructions per second) that may be of application-specific importance, and by the elapsed time such resources were used by the network. In the simplest case, for example, such a meter need measure only the time the PC was made available to the network for processing 4, which can be used to compare with time the PC used the network (which is already normally measured by the provider, as discussed below) to arrive at a net cost; potential locations of such a meter include at a network computer such as a server, at the PC, and at some point on the connection between the two. Throughput of data in any standard terms is another potential measure.

Figure 2:
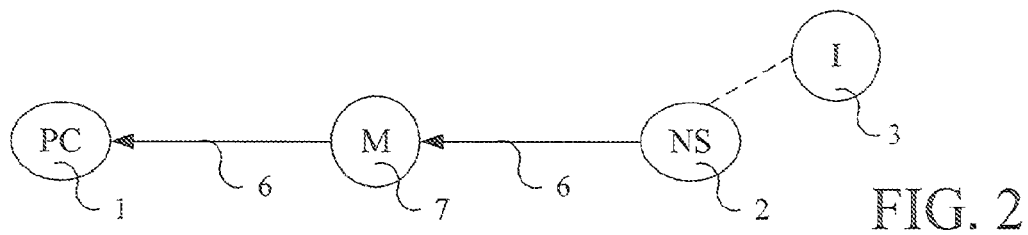
FIG. 2 is a simplified diagram of a section of a computer network, such as the Internet, showing an embodiment of another meter means which measures the flow of network resources, including shared processing, being provided to a typical PC user and a network provider.

In another embodiment, as shown in FIG. 2, there also is a meter device 7 (comprised of hardware and/or software and/or firmware and/or other component) that measures the amount of network resources 6 that are being used by each individual PC 1 user and their associated cost. This includes, for example, time spent doing conventional downloading of data from sites in the network or broadcast from the network 6. Such metering devices currently exist to support billing by the hour of service or type of service is common in the public industry, by providers such as America Online, CompuServe, and Prodigy. The capability of such existing devices is enhanced to include a measure of parallel processing resources that are allocated by the Internet Service Provider or equivalent to an individual PC user from other PC users 6, also measuring simply in time. The net difference in time 4 between the results of meter 5 and meter 7 for a given period provides a reasonable billing basis.

Figure 3:
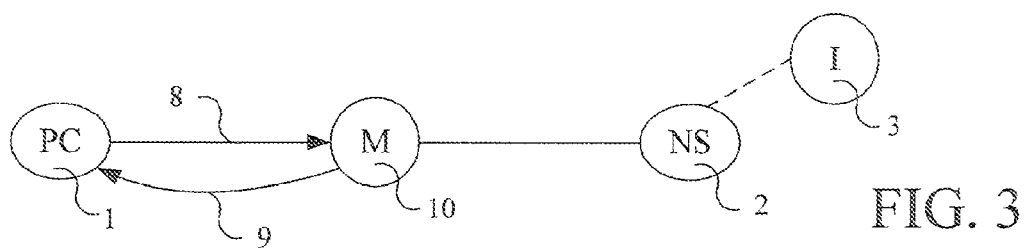
FIG. 3 is a simplified diagram of a section of a computer network, such as the Internet, showing an embodiment of another meter means which, prior to execution, estimates the level of network resources, and their cost, of a shared processing operation requested by a typical PC user from a network provider.

Alternately, as shown in FIG. 3, a meter 10 also estimates to the individual PC user prospectively the amount of network resources needed to fulfill a processing request from the PC user to the network (provider or other level of network control) and associated projected cost, provide a means of approving the estimate by executing the request, and a real-time readout of the cost as it occurs (alternatively, this meter might be done only to alert 9 the PC user that a given processing request 8 falls outside normal, previously accepted parameters, such as level of cost). To take the example of an unusually deep search request, a priority or time limit and depth of search should optimally be criteria or limiting parameters that the user can determine or set with the device.

Preferably, the network involves no payment between users and providers, with the network system (software, hardware, etc) providing an essentially equivalent usage of computing resources by both users and providers (since any network computer operated by either entity can potentially be both a user and provider of computing resources (even simultaneously, assuming multitasking), with potentially an override option by a user (exercised on the basis, for example, of user profile or user's credit line or through relatively instant payment).

Figure 4A:
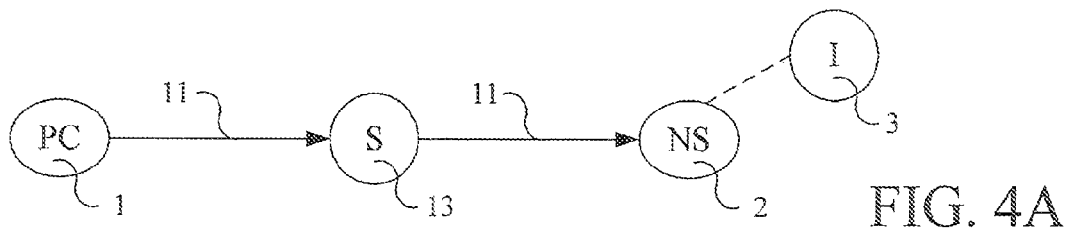
FIG. 4A-4C are simplified diagrams of a section of a computer network, such as the Internet, showing in a sequence of steps an embodiment of a selection means whereby a shared processing request by a PC is matched with a standard preset number of other PC's to execute shared operation.
Figure 4B:
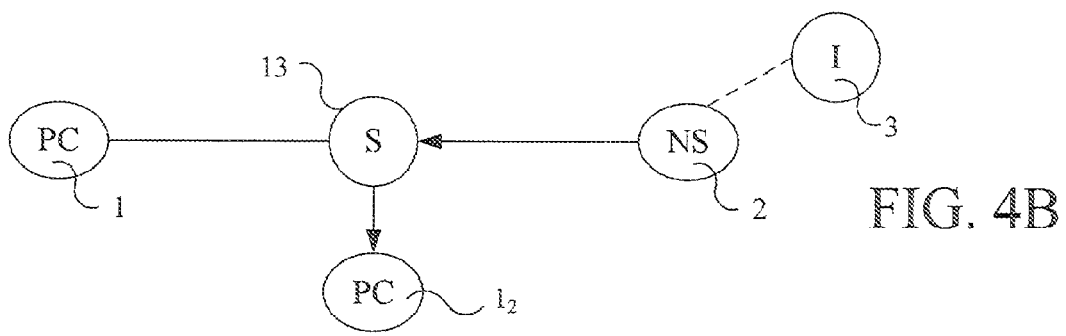
Figure 4C:
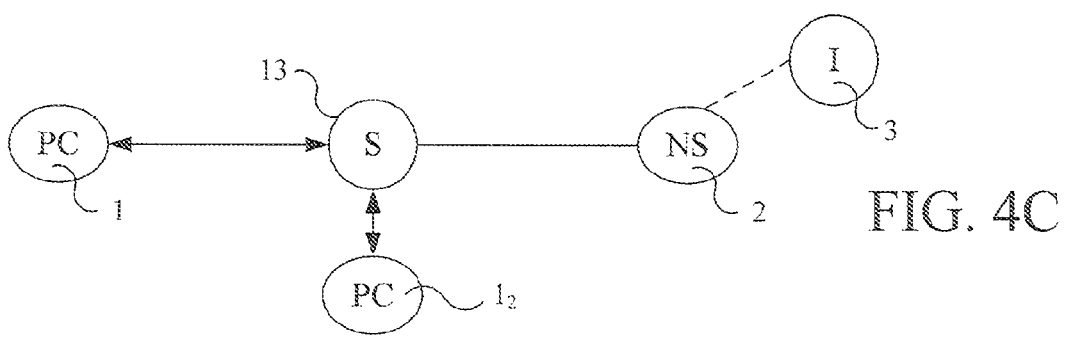

Preferably, as shown in FIGS. 4A-4C, the priority and extent of use of PC and other users can be controlled on a default-to-standard-of-class-usage basis by the network (provider or other) and overridden by the user decision on a basis prescribed by the specific network provider (or by another level of network control). One obvious default basis is to expend up to a PC's or other user's total credit balance with the provider described above and the network provider then to provide further prescribed service on an debt basis up to some set limit for the user; different users might have different limit's based on resources and/or credit history.

A specific category of PC user based, for example, on specific microprocessor hardware owned or leased, might have access to a set maximum number of parallel PC's or microprocessors, with smaller or basic users generally having less access and vice versa. Specific categories of users might also have different priorities for the execution of their processing by the network. A very wide range of specific structural forms between user and provider are possible, both conventional and new, based on unique features of the new network computer system of shared processing resources.

For example, in the simplest case, in an initial system embodiment, as shown in FIG. 4A, a standard PC 1 user request 11 for a use involving parallel processing might be defaulted by system software 13, as shown in FIG. 4B, to the use of only one other essentially identical PC 1$_2$ microprocessor for parallel processing or multitasking, as shown in FIG. 4C; larger standard numbers of PC microprocessors, such as about three PC's at the next level, as shown in later FIG. 10G (which could also illustrate a PC 1 user exercising an override option to use a level of services above the default standard of one PC microprocessor, presumably at extra cost), for a total of about four, then about 8, about 16, about 32, about 64 and so on, or virtually any number in between, is made available as the network system is upgraded in simple phases over time, as well as the addition of sophisticated override options. As the phase-in process continues, many more PC microprocessors can be made available to the standard PC user (virtually any number), preferably starting at about 128, then about 256, then about 512, then about 1024 and so on over time, as the network and all of its components are gradually upgraded to handle the increasing numbers. System scalability at even the standard user level is essentially unlimited over time.

Preferably, for most standard PC users (including present and future equivalents and successors), connection to the Internet (or present or future equivalents or successors like the MetaInternet) can be at no cost to PC users, since in exchange for such Internet access the PC users can generally make their PC, when idle, available to the network for shared processing. Preferably, then, competition between Internet Service Providers (including present and future equivalents and successors) for PC user customers can be over such factors as the convenience and quality of the access service provided and of shared processing provided at no addition cost to standard PC users, or on such factors as the level of shared processing in terms, for example of number of slave PC's assigned on a standard basis to a master PC. The ISP's can also compete for parallel processing operations, from inside or outside the ISP Networks, to conduct over their networks.

Figure 5A:
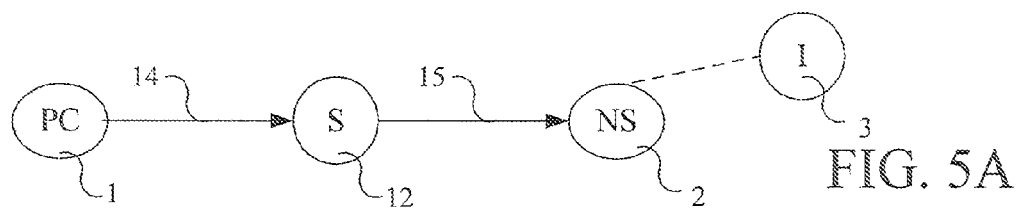
FIGS. 5A and 5B are simplified diagrams of a section of a computer network, such as the Internet, showing an embodiment of a control means whereby the PC, when idled by its user, is made available to the network for shared processing operations.
Figure 5B:
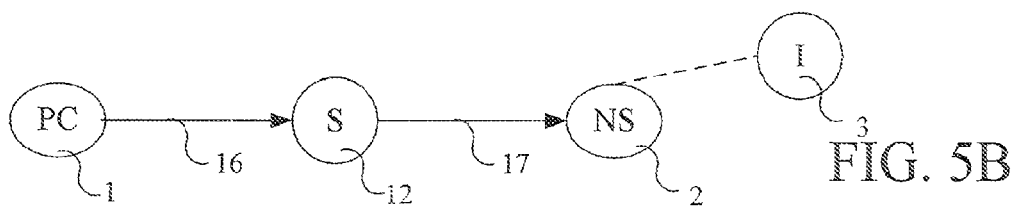

In addition, as shown in FIGS. 5A-5B, in another embodiment there is a (hardware and/or software and/or firmware and/or other) controlling device to control access to the user's PC by the network. In its simplest form, such as a manually activated electromechanical switch, the PC user could set this controller device to make the PC available to the network when not in use by the PC user. Alternatively, the PC user could set the controller device to make the PC available to the network whenever in an idle state, however momentary, by making use of multitasking hardware and/or software and/or firmware and/or other component (broadcast or "push" applications from the Internet or other network could still run in the desktop background). Or, more simply, as shown in FIG. 5A, whenever the state that all user applications are closed and the PC 1 is available to the network 14 (perhaps after a time delay set by the user, like that conventionally used on Screensaver software) is detected by a software controller device 12 installed in the PC, the device 12 signals 15 the network computer such as a server 2 that the PC available to the network, which could then control the PC 1 for parallel processing or multitasking by another PC. Such shared processing can continue until the device 12 detects the an application being opened 16 in the first PC (or at first use of keyboard, for quicker response, in a multitasking environment), when the device 12 signals 17 the network computer such as a server 2 that the PC is no longer available to the network, as shown in FIG. 5B, so the network can then terminate its use of the first PC.

Figure 6:
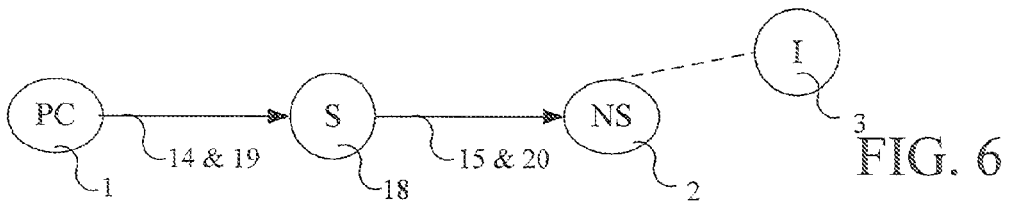
FIG. 6 is a simplified diagram of a section of a computer network, such as the Internet, showing an embodiment of a signal means whereby the PC, when idled by its user, signals its availability to the network for shared processing operations.

In a preferred embodiment, as shown in FIG. 6, there is a (hardware and/or software and/or firmware and/or other component) signaling device 18 for the PC 1 to indicate or signal 15 to the network the user PC's availability 14 for network use (and whether full use or multitasking only) as well as its specific (hardware/software/firmware/other components) configuration 20 (from a status 19 provided by the PC) in sufficient detail for the network or network computer such as a server 2 to utilize its capability effectively. In one embodiment, the transponder device is resident in the user PC and broadcast its idle state or other status (upon change or periodically, for example) or respond to a query signal from a network device.

Figure 7:
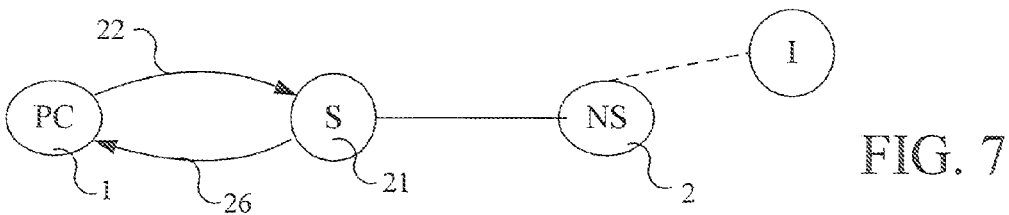
FIG. 7 is a simplified diagram of a section of a computer network, such as the Internet, showing an embodiment of a receiver and/or interrogator means whereby the network receives and/or queries the availability for shared processing status of a PC within the network.

Also, in another embodiment, as shown in FIG. 7, there is a (hardware/software and/or firmware and/or other component) transponder device 21 resident in a part of the network (such as network computer, switch, router, or another PC, for examples) that receives 22 the PC device status broadcast and/or queries 26 the PC for its status, as shown in FIG. 7.

Figure 8:
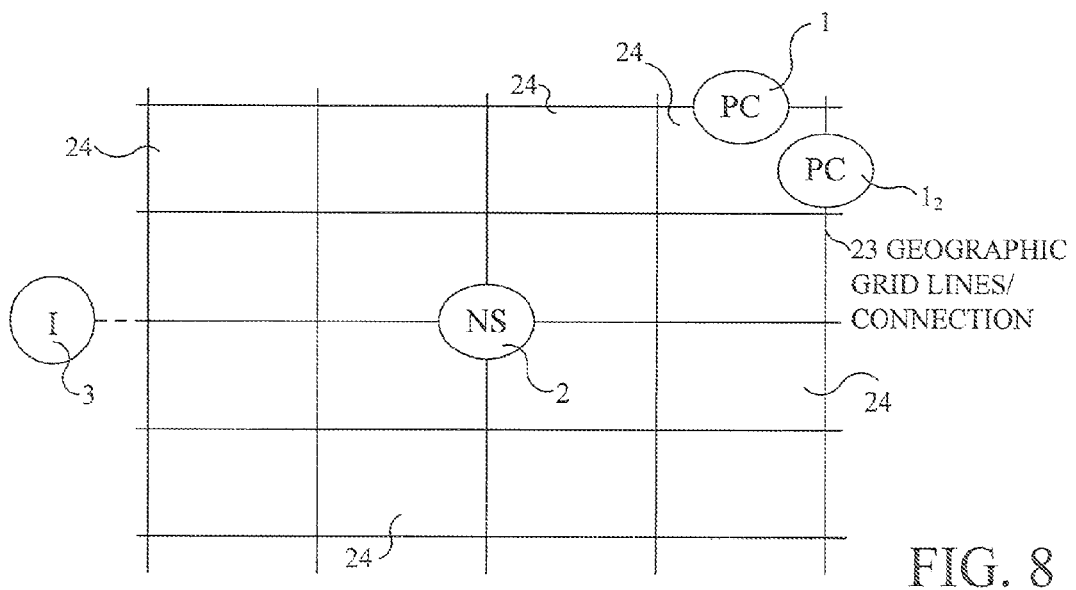
FIG. 8 is a simplified diagram of a section of a computer network, such as the Internet, showing an embodiment of a selection and/or utilization means whereby the network locates available PC's in the network that are located closest to each other for shared processing.

In one embodiment, as shown in FIG. 8, the network also has resident in a part of its hardware and/or software (and/or firmware and/or other components) a capacity such as to allow it to most effectively select and utilize the available user PC's to perform parallel processing initiated by PC users or the network providers or others. To do so, the network should have the (hardware and/or software and/or firmware and/or other component) capability of locating each PC accurately at the PC's position on the geographic grid lines/connection means 23 so that parallel processing occurs between PC's (PC 1 and PC $1_2$) as close together as possible, which should not be difficult for PC's at fixed sites with a geographic location, customarily grouped together into cells 24, as shown in FIG. 8, but which requires an active system for any wireless microprocessor to measure its distance from its network relay site, as discussed below in FIG. 14.

Figure 9:
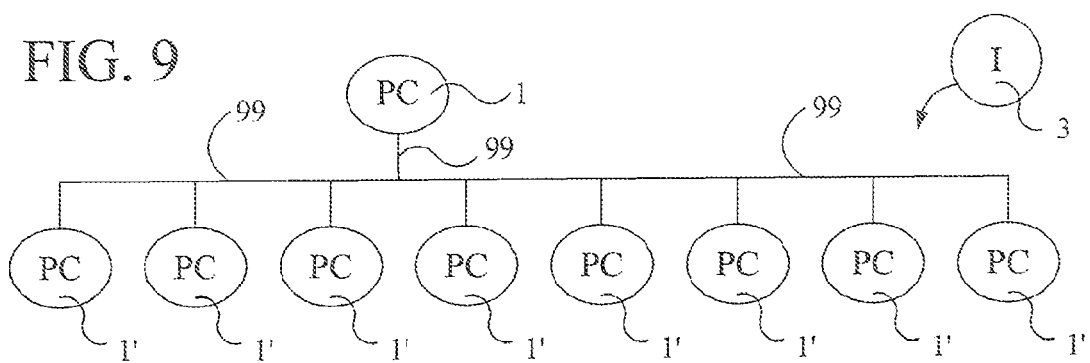
FIG. 9 is a simplified diagram of a section of a computer network, such as the Internet, showing an embodiment of a system architecture for conducting a request imitated by a PC for a search using parallel processing means that utilizes a number of networked PC's.

One of the primary capabilities of the Internet (or Internet II or successor, like the MetaInternet) or WWW network computer is to facilitate searches by the PC user or other user. As shown in FIG. 9, searches are particularly suitable to multiple processing, since, for example, a typical search is to find a specific Internet or WWW site with specific information. Such site searches can be broken up geographically, with a different PC processor 1' allocated by the network communicating through a wired means 99 as shown (or wireless connections) to search each area, the overall area being divided into eight separate parts, as shown, which are preferably about equal, so that the total search would be about ⅛ as long as if one processor did it alone (assuming the PC 1 microprocessor provides control only and not parallel processing, which may be preferable in some case).

As a typical example, a single PC user might need 1,000 minutes of search time to find what is requested, whereas the network computer, using multiple PC processors, might be able to complete the search in 100 minutes using 10 processors, or 10 minutes using 100 processors or 1 minute using 1,000 processors (or even 1 second using 60,000 processors); assuming performance transparency, which should be achievable, at least over time. The network's external parallel processing is optimally completely scalable, with virtually no theoretical limit.

The above examples also illustrates a tremendous potential benefit of network parallel processing. The same amount of network resources, 60,000 processor seconds, was expended in each of the equivalent examples. But by using relatively large multiples of processors, the network can provide the user with relatively immediate response with no difference in cost (or relatively little difference)—a major benefit. In effect, each PC user linked to the network providing external parallel processing becomes, in effect, a virtual supercomputer! As discussed below, supercomputers can experience a similar quantum leap in performance by employing a thousand-fold (or more) increase in microprocessors above current levels.

Such power will likely be required for any effective searches in the World Wide Web (WWW). WWW is currently growing at a rate such that it is doubling every year, so that searching for information within the WWW will become geometrically more difficult in future years, particularly a decade hence, and it is already a very significant difficulty to find WWW sites of relevance to any given search and then to review and analyze the contents of the site.

So the capability to search with massive parallel processing will be required to be effective and can dramatically enhance the capabilities of scientific, technological and medical researchers.

Such enhanced capabilities for searching (and analysis) can also fundamentally alter the relationship of buyers and sellers of any items and/or services. For the buyer, massive parallel network processing can make it possible to find the best price, worldwide, for any product or the most highly rated product or service (for performance, reliability, etc.) within a category or the best combination of price/performance or the highest rated product for a given price point and so on. The best price for the product can include best price for shipping within specific delivery time parameters acceptable to the buyer.

For the seller, such parallel processing can drastically enhance the search, worldwide, for customers potentially interested in a given product or service, providing very specific targets for advertisement. Sellers, even producers, can know their customers directly and interact with them directly for feedback on specific products and services to better assess customer satisfaction and survey for new product development.

Similarly, the vastly increased capability provided by the system's shared parallel processing can produce major improvements in complex simulations like modeling worldwide and local weather systems over time, as well as design and testing of any structure or product, from airliners and skyscrapers, to new drugs and to the use of much more sophisticated artificial intelligence (AI) in medical treatment and in sorting through and organizing the PC users voluminous input of electronic data from "push" technologies. Improvements in games also result, especially in terms of realistic simulation and realtime interactivity.

As is clear from the examples, the Internet or WWW network computer system like the MetaInternet can potentially put into the hands of the PC user an extraordinary new level of computer power vastly greater than the most powerful supercomputer existing today. The world's total of microchips is already about 350 billion, of which about 15 billion are microprocessors of some kind (most are fairly simple "appliance" type running wrist watches, televisions, cameras, cars, telephones, etc). Assuming growth at its current rates, in a decade the Internet/Internet II/WWW could easily have a billion individual PC users, each providing a average total of at least 10 highly sophisticated microprocessors (assuming PC's with at least 4 microprocessors (or more, such as 16 microprocessors or 32, for example) and associated other handheld, home entertainment, and business devices with microprocessors or digital processing capability, like a digital signal processor or successor devices). That results in a global computer a decade from now made of at least 10 billion microprocessors, interconnected by electromagnetic wave means at speeds approaching the speed of light.

In addition, if the exceptionally numerous "appliance" microprocessors noted above, especially those that operate now intermittently like personal computers, are designed to the same basic consensus industry standard as parallel microprocessors for PC's (or equivalents or successors) or for PC "systems on a chip" discussed later in FIG. 10A-H, and if also connected by broad bandwidth means such as fiber optic cable or equivalent wireless, then the number of parallel processors potentially available can increase roughly about 10 times, for a net potential "standard" computing performance of up to 10,000 times current performance within fifteen years, exclusive of Moore's Law routine increases. Moreover, in a environment where all currently intermittently operating microprocessors followed the same basic design standards, then although the cost per microprocessor increases somewhat, especially initially, the net cost of computing for all users falls drastically due to the general performance increase due to the use of otherwise idle "appliance" microprocessors. Therefore, the overall system cost reduction compels a transformation of virtually all such microprocessors, which are currently specialty devices known as application-specific integrated circuits (ASICs), into general microprocessors (like PC's), with software and firmware providing most of their distinguishing functionality.

To put this in context, a typical supercomputer today utilizing the latest PC microprocessors has less than a hundred. Using network linkage to all external parallel processing, a peak maximum of perhaps 1 billion microprocessors can be made available for a network supercomputer user, providing it with the power 10,000,000 times greater than is available using current conventional internal parallel processing supercomputers (assuming the same microprocessor technology). Because of it's virtually limitless scalability mentioned above, resources made available by the network to the supercomputer user or PC user can be capable of varying significantly during any computing function, so that peak computing loads can be met with effectively whatever level of resources are necessary.

In summary, regarding monitoring the net provision of power between PC and network, FIGS. 1-9 show embodiments of a system for a network of computers, including personal computers, comprising: means for network services including browsing functions, as well as shared computer processing such as parallel processing, to be provided to the personal computers within the network; at least two personal computers; means for at least one of the personal computers, when idled by a personal user, to be made available temporarily to provide the shared computer processing services to the network; and means for monitoring on a net basis the provision of the services to each the personal computer or to the personal computer user. In addition, FIGS. 1-9 show embodiments including where the system is scalar in that the system imposes no limit to the number of the personal computers, including at least 1024 personal computers; the system is scalar in that the system imposes no limit to the number of personal computers participating in a single shared computer processing operation, including at least 256 personal computers; the network is connected to the Internet and its equivalents and successors, so that the personal computers include at least a million personal computers; the network is connected to the World Wide Web and its successors; the network includes at least one network server that participates in the shared computer processing; the monitoring means includes a meter device to measure the flow of computing power between the personal computers and the network; the monitoring means includes a means by which the personal user of the personal computer is provided with a prospective estimate of cost for the network to execute an operation requested by the personal user prior to execution of the operation by the network; the system has a control means by which to permit and to deny access to the personal computers by the network for shared computer processing; access to the personal computers by the network is limited to those times when the personal computers are idle; and the personal computers having at least one microprocessor and communicating with the network through a connection means having a speed of data transmission that is at least greater than a peak data processing speed of the microprocessor.

Also, relative to maintaining a standard cost, FIGS. 1-9 show embodiments of a system for a network of computers, including personal computers, comprising: means for network services including browsing functions, as well as shared computer processing such as parallel processing, to be provided to the personal computers within the network; at least two personal computers; means for at least one of the personal computers, when idled by a personal user, to be made available temporarily to provide the shared computer processing services to the network; and means for maintaining a standard cost basis for the provision of the services to each personal computer or to the personal computer user. In addition, FIGS. 1-9 show embodiments including where the system is scalar in that the system imposes no limit to the number of personal computers, including at least 1,024 personal computers; the system is scalar in that the system imposes no limit to the number of the personal computers participating in a single shared computer processing operation, including at least 256 personal computers; the network is connected to the Internet and its equivalents and successors, so that the personal computers include at least a million personal computers; the standard cost is fixed; the fixed standard cost is zero; the means for maintaining a standard cost basis includes the use of making available a standard number of personal computers for shared processing by personal computers; the network is connected to the World Wide Web and its successors; the personal user can override the means for maintaining a standard cost basis so that the personal user can obtain additional network services; the system has a control means by which to permit and to deny access to the personal computers by the network for shared computer processing; the personal computers having at least one microprocessor and communicating with the network through a connection means having a speed of data transmission that is at least greater than a peak data processing speed of the microprocessor.

Browsing functions generally include functions like those standard functions provided by current Internet browsers, such as Microsoft Explorer 3.0 or 4.0 and Netscape Navigator 3.0 or 4.0, including at least access to searching World Wide Web or Internet sites, exchanging E-Mail worldwide, and worldwide conferencing; an intranet network uses the same browser software, but might not include access to the Internet or WWW. Shared processing includes parallel processing and multitasking processing involving more than two personal computers, as defined above. The network system is entirely scalar, with any number of PC microprocessors potentially possible.

As shown in FIGS. 10A-10F, to deal with operational and security issues, it may be optimal for individual users to have one microprocessor or equivalent device that is designated, permanently or temporarily, to be a master 30 controlling device (comprised of hardware and/or software and/of firmware and/or other component) that remains unaccessible (preferably using a hardware and/or software and/or firmware and/or other component firewall 50) directly by the network but which controls the functions of the other, slave microprocessors 40 when the network is not utilizing them.

Figure 10A:
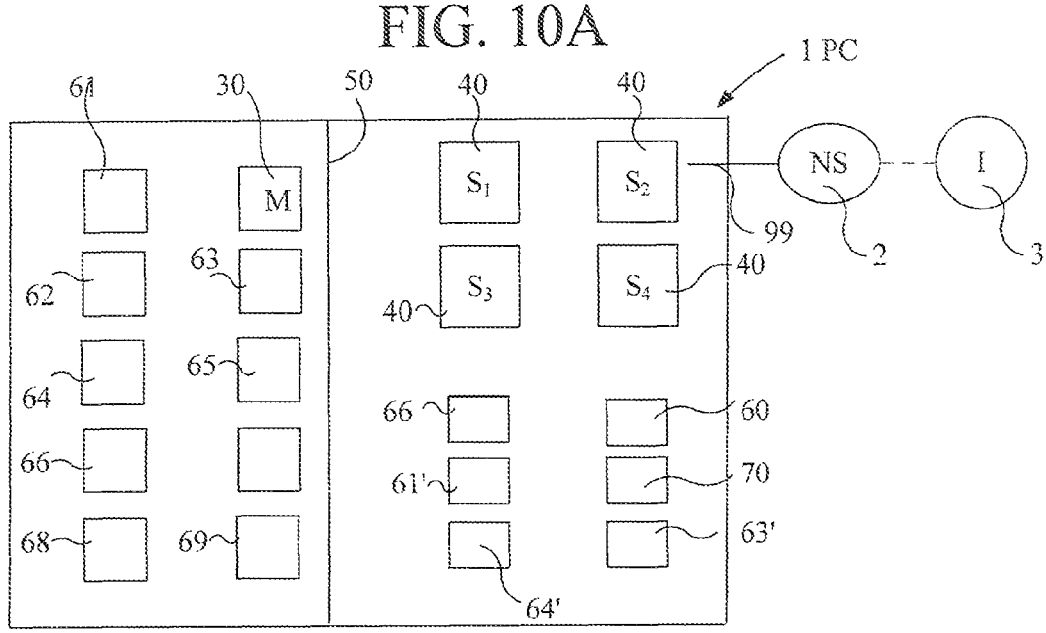
FIGS. 10A-10Q are simplified diagrams of a section of a computer network, such as the Internet, showing an embodiment of a system architecture utilizing a firewall to separate that part of a networked PC (including a system reduced in size to a microchip) that is accessible to the network for shared processing from a part that is kept accessible only to the PC user; also showing the alternating role that preferably each PC in the network can play as either a master or slave in a shared processing operation involving one or more slave PC's in the network; and showing a home or business network system, which can be configured as an Intranet; in addition, showing PC and PC microchips controlled by a controller (including remote) with limited or no processing capability; and showing PC and PC microchips in which a firewall 50 is can be reconfigured by a PC user.

For example, as shown in FIG. 10A, a typical PC 1 might have four or five microprocessors (even on a single microprocessor chip), with one master 30 and three or four slaves 40, depending on whether the master 30 is a controller exclusively (through different design of any component part), requiring four slave microprocessors 40 preferably; or the master microprocessor 30 has the same or equivalent microprocessing capability as a slave 40 and multiprocesses in parallel with the slave microprocessors 40, thereby requiring only three slave microprocessors 40, preferably. The number of PC slave microprocessors 40 can be increased to virtually any other number, such as at least about eight, about 16, about 32, about 64, about 128, about 256, about 512, about 1024, and so on (these multiples are preferred as conventional in the art, but not clearly required; the PC master microprocessors 30 can also be increased. Also included is the preferred firewall 50 between master 30 and slave 40 microprocessors. As shown in preceding FIGS. 1-9, the PC 1 in FIG. 10A is preferably connected to a network computer 2 and to the Internet or WWW or present or future equivalent or successor 3, like the MetaInternet.

Other typical PC hardware components such as hard drive 61, floppy diskette 62, CD-ROM 63, DVD 64, Flash memory 65, RAM 66, video or other display 67, graphics card 68, and sound card 69, together with the software and/or firmware stored on or for them, can be located on either side of the preferred firewall 50, but such devices as the display 67, graphics card 68 and sound card 69 and those devices that both read and write and have non-volatile memory (retain data without power and generally have to written over to erase), such as hard drive 62, Flash memory 65, floppy drive 62, read/write CD-ROM 63 or DVD 64 are preferred to be located on the PC user side of the firewall 50, where the master microprocessor is also located, as shown in FIG. 10A, for security reasons primarily.

Alternately, any of these devices that are duplicative (or for other exceptional needs), like a second hard drive 61', can be located on the network side of the firewall 50. RAM 66 or equivalent memory, which typically is volatile (data is lost when power is interrupted), should generally be located on the network side of the firewall 50. However, read-only memory devices such as most current CD drives (CD-ROM's) 63' or DVD's (DVD-ROM) 64' can be safely located on the network side of the firewall 50, since the data on those drives cannot be altered by network users; preemptive control of use preferably remains with the PC user.

However, at least a portion of RAM is can be kept on the Master 30 microprocessor side of the firewall 50, so that the PC user can use retain the ability to use a core of user PC 1 processing capability entirely separate from any network processing. If this capability is not desired, then the master 30 microprocessor can be moved to the network side of the firewall 50 and replaced with a simpler controller on the PC 1 user side, like the master remote controller 31 discussed below and shown in FIG. 10I.

And the master microprocessor 30 might also control the use of several or all other processors 60 owned or leased by the PC user, such as home entertainment digital signal processors 70, especially if the design standards of such microprocessors in the future conforms to the requirements of network parallel processing as described above. In this general approach, the PC master processor uses the slave microprocessors or, if idle (or working on low priority, deferable processing), make them available to the network provider or others to use. Preferably, wireless connections 100 are extensively used in home or business network systems, including use of a master remote controller 31 without (or with) microprocessing capability, with preferably broad bandwidth connections such as fiber optic cable connecting directly to at least one component such as a PC 1, shown in a slave configuration, of the home or business personal network system; that preferred connection links the home system to the network 2 such as the Internet 3, as shown in FIG. 10I.

Figure 10B:
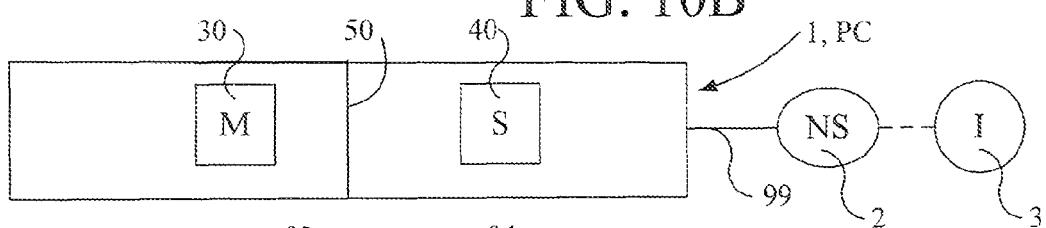

In the simplest configuration, as shown in FIG. 10B, the PC 1 has a single master microprocessor 30 and a single slave microprocessor 40, preferably separated by a firewall 50, with both processors used in parallel or multitasking processing or with only the slave 40 so used, and preferably connected to a network computer 2 and Internet 3 (and successors like the MetaInternet). Virtually any number of slave microprocessors 40 is possible. The other non-microprocessor components shown in FIG. 10A above might also be included in this simple FIG. 10B configuration.

Figure 10C:
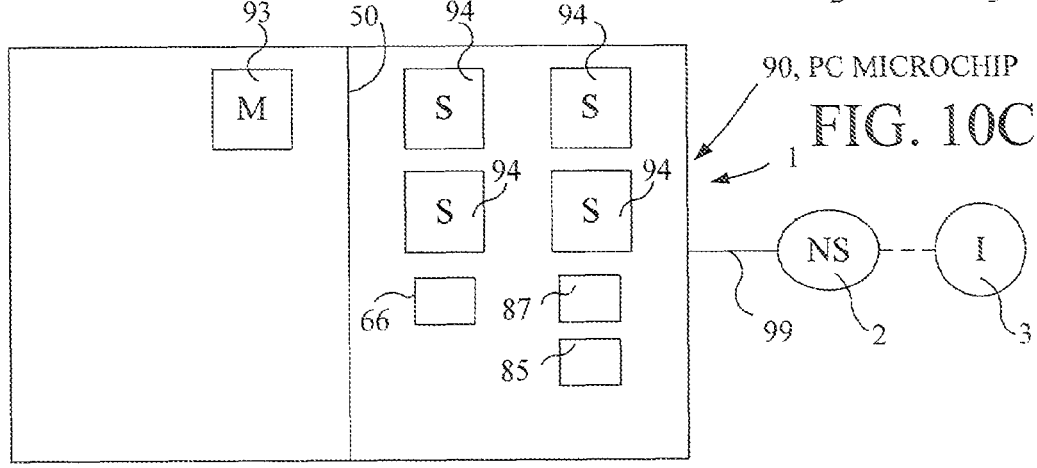

Preferably, as shown in FIG. 10C, microprocessors 90 are expected to integrate most or all of the other necessary computer components (or their present or future equivalents or successors), like a PC's memory (RAM 66, graphics 82, sound 83, power management 84, network communications 85, and video processing 86, possibly including modem 87, flash bios 88, and other components or present or future equivalents or successors) and internal bus, on a single chip 90 (silicon, plastic, or other), known in the industry as "system on a chip". Such a PC microchip 90 preferably has the same architecture as that of the PC 1 shown above in FIG. 10A: namely, a master control and/or processing unit 93 and one or more slave processing units 94 (for parallel or multitasking processing by either the PC 1 or the Network 2), preferably separated by a firewall 50 and preferably connected to a network computer 3 and the Internet 3 and successors like the MetaInternet.

Existing PC components with mechanical components like hard drive 61, floppy or other removable diskette 62, CD-ROM 63 and DVD 64, which are mass storage devices that will likely not become an integral part of a PC "system of a chip" preferably, of course, still is capable of connection to a single PC micro chip 90 and control by a single PC master unit 93.

Figure 10D:
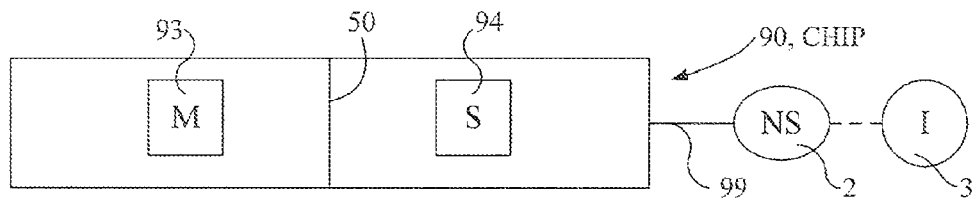

In the simplest case, as shown in FIG. 10D, the chip 90 has a single master unit 93 and at least one slave unit 94 (with the master having a controlling function only or a processing function also), preferably separated by a firewall 50 and preferably connected to a network computer 3 and the Internet 3 (and successors like the MetaInternet).

Figure 10E:
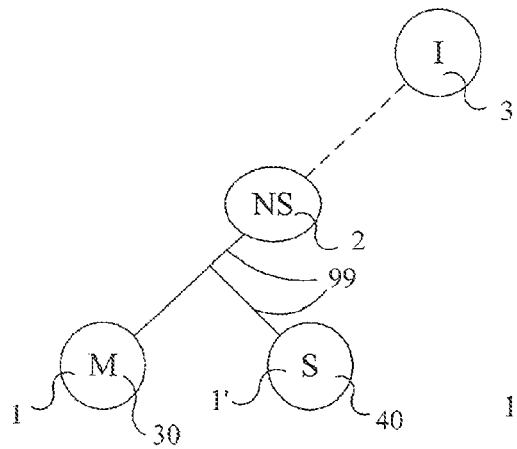
Figure 10F:
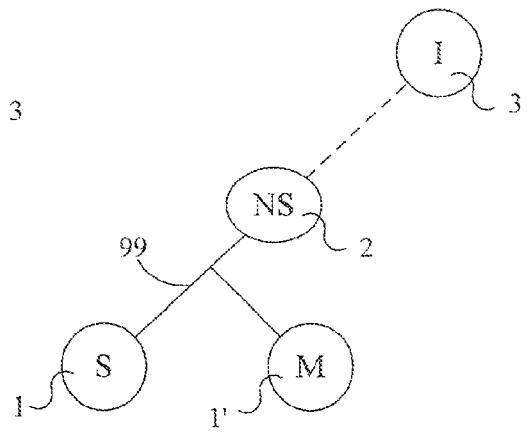

As noted in the second paragraph of the introduction to the background of the invention, in the preferred network invention, any computer can potentially be both a user and provider, alternatively—a dual mode. Consequently, any PC 1 within the network 2, preferably connected to the Internet 3 (and successors like the MetaInternet), can be temporarily a master PC 30 at one time initiating a parallel or multitasking processing request to the network 2 for execution by at least one slave PC 40, as shown in FIG. 10E. At another time the same PC 1 can become a slave PC 40 that executes a parallel or multitasking processing request by another PC 1' that has temporarily assumed the function of master 30, as shown in FIG. 10F. The simplest approach to achieving this alternation is for both master and slave versions of the parallel processing software to be loaded in each or every PC 1 that is to share in the parallel processing, so each PC 1 has the necessary software means, together with minor operation modifications, such as a switching means by which a signal request for parallel processing initiated by one PC 1 user using master software is transmitted to at least a second PC 1, triggering its slave software to respond to initiate parallel processing.

Figure 10G:
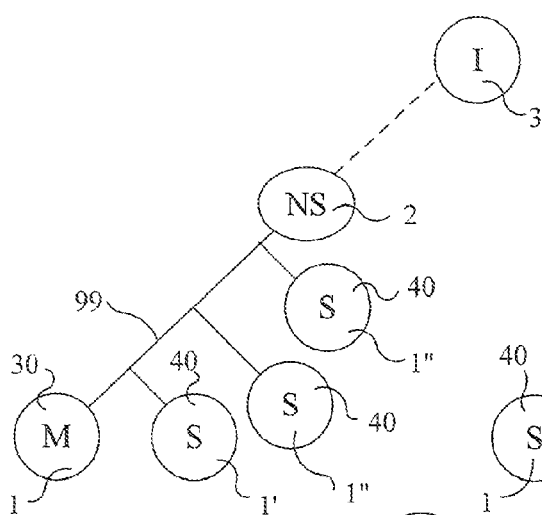
Figure 10H:
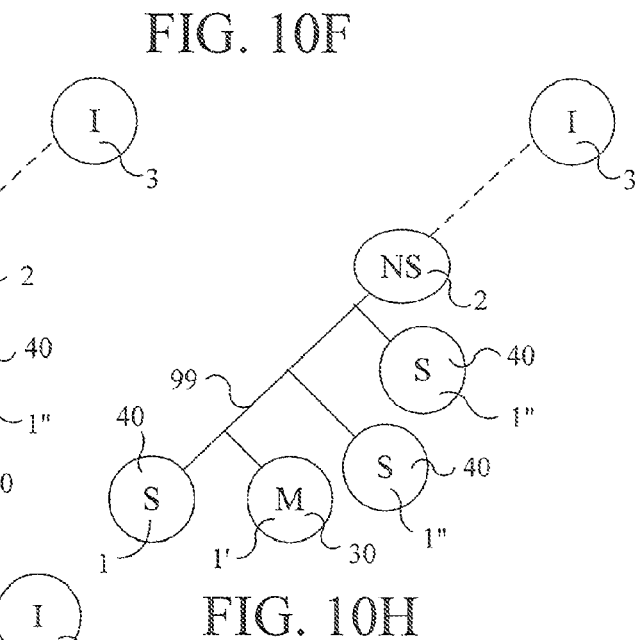
Figure 10I:
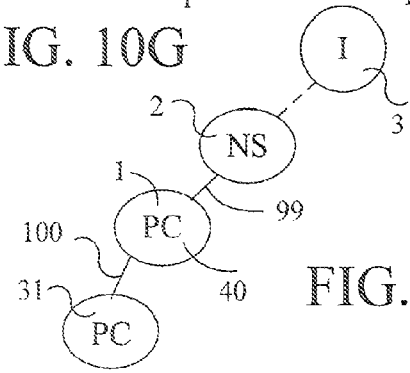

Figure As shown in FIGS. 10G and 10H, which are parallel to FIGS. 10E and 10F, the number of PC slave processors 40 can be increased to any virtually other number, such as at least about 4; the processing system is completely scalar, so that further increases can occur to about eight, about 16, about 32, about 64, about 128, about 256, about 512, about 1024, and so on (these multiples indicated are preferred as conventional in the art, but not mandatory); the PC master microprocessors 30 can also be increased.

Figure 10J:
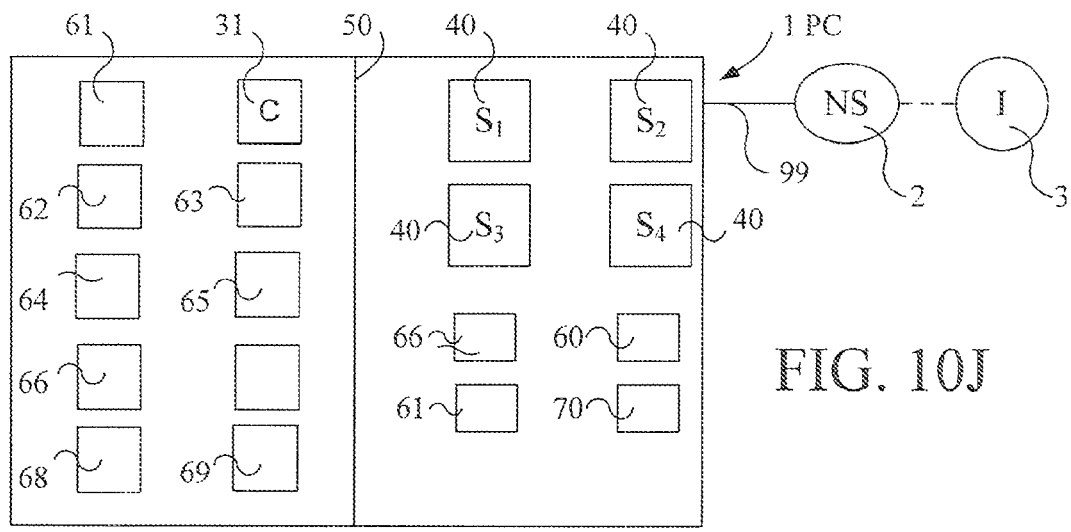
Figure 10K:
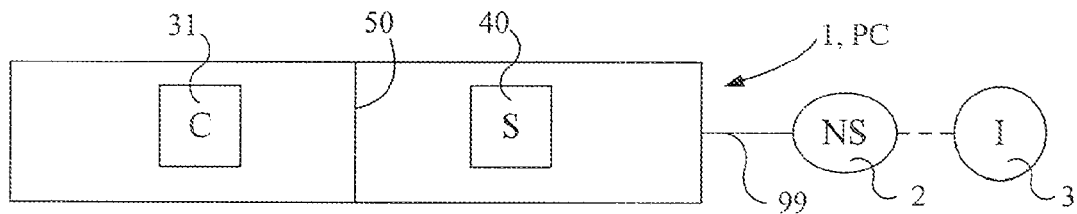
Figure 10L:
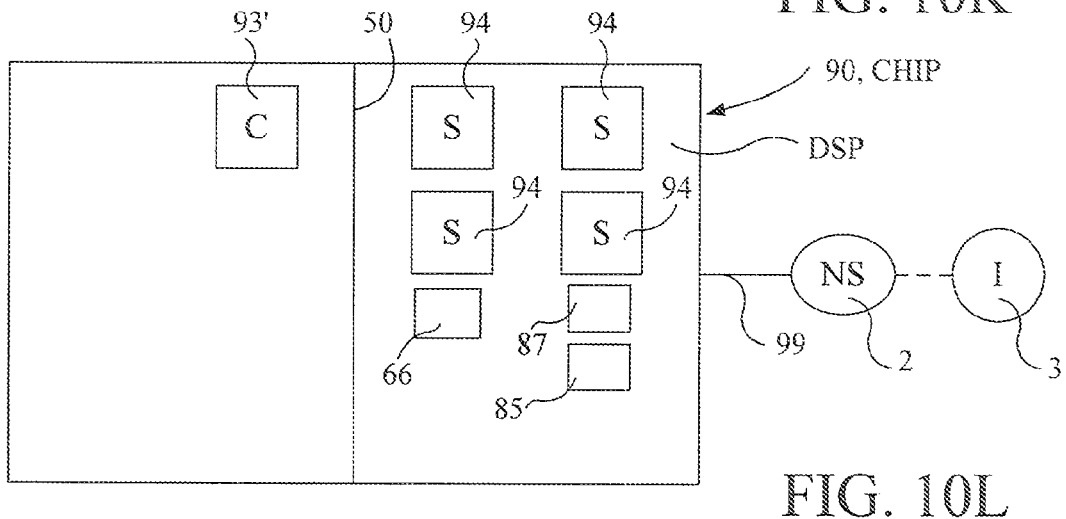
Figure 10M:
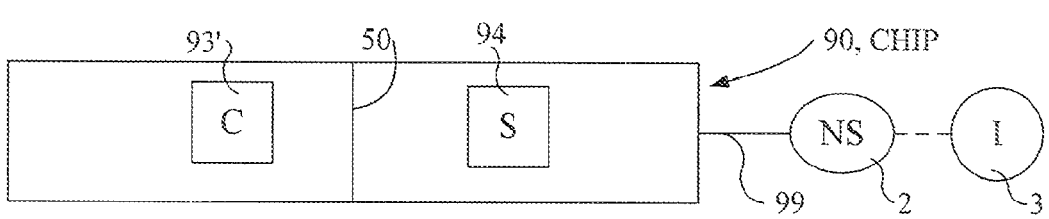

In summary, as noted above relative to FIG. 10I, a PC 1 can function as a slave PC 40 and be controlled by a master controller 31, which can be remote and which preferably can have limited or no microprocessing capability, but can as well have similar or greater capability. As shown in FIGS. 10J and 10K, such a master controller 31 is located on the PC user side of the firewall 50, under the control of the PC user, while the microprocessors 40 reside on the network side of the firewall 50. The master controller 31 preferably receives input from the PC user by local means such as keyboard, microphone, videocam or future hardware and/or software and/or firmware or other equivalent or successor means (as does a master processor 40); in addition, remote access by telephone, cable, wireless or other connection might also be enabled by a hardware and/or software and/or firmware and/or other means with suitable security such as password controlled access. Similarly, as shown in FIGS. 10L and 10M, relative to a PC "system on a chip" a master controller unit 93' (which could be capable of being accessed by the PC user through a remote controller 31) with only a controlling capability is located on the PC user side of the firewall 50, under the control of the PC user (and potentially including control by a network systems administrator), while the slave processor units 94 reside on the network side of the firewall 50.

Figure 10N:
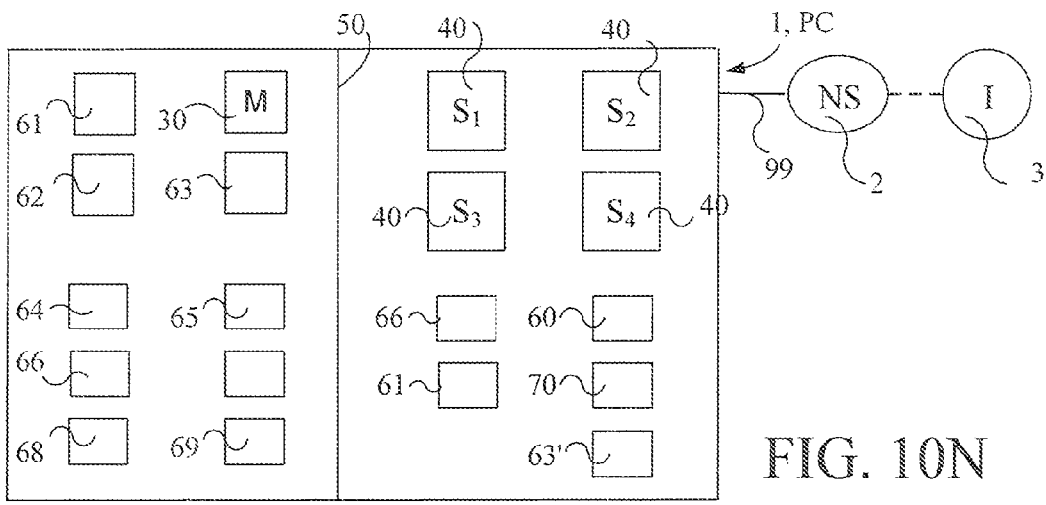

FIGS. 10N and 10O show PC 1 with a firewall 50 that is configurable through either hardware and/or software and/or firmware and/or other means; software configuration are easiest and most typical, but active motherboard hardware configuration is possible and may present some security advantages, including as use of manual or electromechanical or other switches or locks. FIG. 10N shows a CD-ROM 63' that has been placed by a PC user on the network side of a firewall 50 from a previous position on the PC user side of a firewall 50, which was shown in FIG. 10A. Preferably, the settings of a firewall 50 can default to those that safely protect the PC 1 from uncontrolled access by network users, but with capability for the relatively sophisticated PC user to override such default settings and yet with proper safeguards to protect the unsophisticated user from inadvertently doing so; configuration of a firewall 50 might also be actively controlled by a network administrator in a local network like that of a business, where a PC user may not be owner or leaser of the PC being used, either by remote access on the network or with a remote controller 31.

Figure 10P:
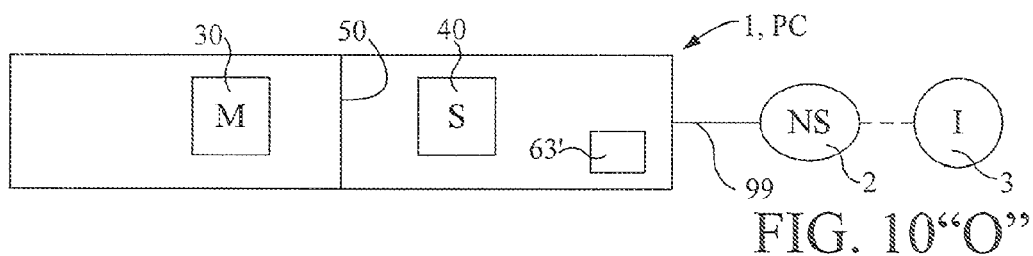
Figure 10P:
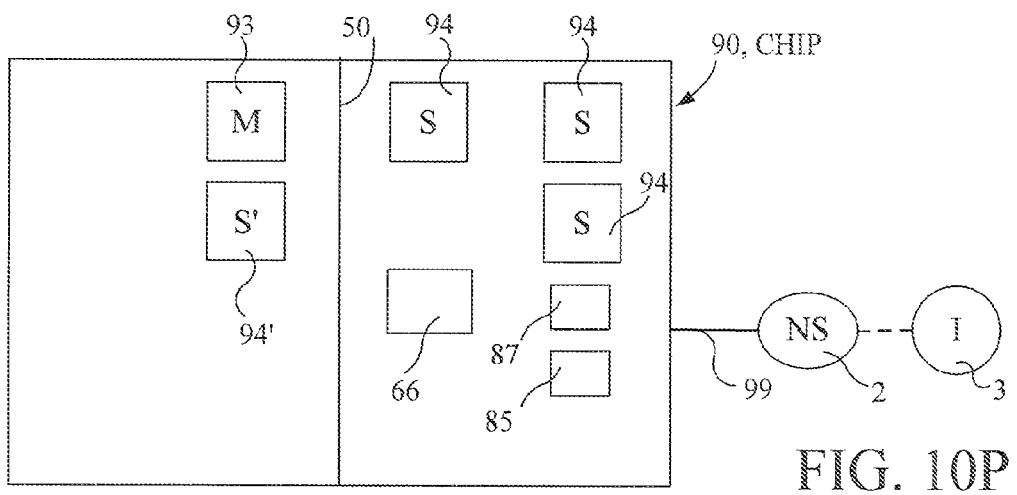
Figure 10Q:
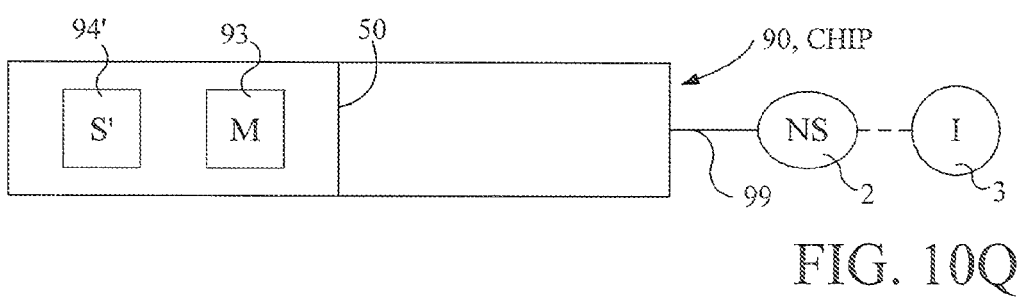

Similarly, FIGS. 10P and 10Q show a PC "system of a chip" 90 with a firewall 50 that is configurable through either hardware and/or software and/or firmware and/or other means; software configuration is easiest and most typical. Active configuration of the integrated circuits of the PC microchip 90 is also possible and may present some speed and security advantages. Such direct configuration of the circuits of the microchip 90 to establish or change in its firewall 50 could be provided by the use of field-programmable gate arrays (or FPGA's) or their future equivalents or successors; microcircuit electromechanical or other switches or locks can also be used potentially. In FIG. 10P, for example, slave processing unit 94' has been moved to the PC user side of a firewall 50 from a network side position shown in FIGS. 10C and 10L. Similarly, FIG. 10Q shows the same active configuration of chip circuit using FPGA's for the simplest form of multiprocessing microchip 90 with a single slave unit 94', transferring its position to the PC user's side of a firewall 50 from a network side shown in FIGS. 10M and 10D.

In summary, relative to the use of master/slave computers, FIGS. 10A-10I show embodiments of a system for a network of computers, including personal computers, comprising: at least two personal computers; means for at least one personal computer, when directed by its personal user, to function temporarily as a master personal computer to initiate and control the execution of a computer processing operation shared with at least one other the personal computer in the network; means for at least one other personal computer, when idled by its personal user, to be made available to function temporarily as at least one slave personal computer to participate in the execution of a shared computer processing operation controlled by the master personal computer; and means for the personal computers to alternate as directed between functioning as a master and functioning as a slave in the shared computer processing operations. In addition, FIG. 10A-10H show embodiments including wherein the system is scalar in that the system imposes no limit to the number of personal computers; for example, the system can include at least 256 said personal computers; the system is scalar in that the system imposes no limit to the number of personal computers participating in a single shared computer processing operation, including at least 256 said personal computers, for example; the network is connected to the Internet and its equivalents and successors, so that personal computers include at least a million personal computers, for example; the shared computer processing is parallel processing; the network is connected to the World Wide Web and its successors; a means for network services, including browsing and broadcast functions, as well as shared computer processing such as parallel processing, are provided to said personal computers within said network; the network includes at least one network server that participates in the shared computer processing; the personal computers include a transponder or equivalent or successor means so that a master personal computer can determine the closest available slave personal computers; the closest available slave personal computer is compatible with the master personal computer to execute said shared computer processing operation; the personal computers having at least one microprocessor and communicating with the network through a connection means preferably having a speed of data transmission that is at least greater than a peak data processing speed of the microprocessor.

The preferred use of the firewall 50, as described above in FIGS. 10A-10I, provides a solution to an important security problem by preferably completely isolating host PC's 1 that are providing slave microprocessors to the network for parallel or other shared processing functions from any capability to access or retain information about any element about that shared processing. In addition, of course, the firewall 50 provides security for the host PC against intrusion by outside hackers; by reducing the need for encryption and authentication, the use of firewalls 50 can provide a relative increase in computing speed and efficiency. In addition to computers such as personal computers, the firewall 50 described above could be used in any computing device included in this application's above definition of personal computers, including those with "appliance"-type microprocessors, such as telephones, televisions or cars, as discussed above.

In summary, regarding the use of firewalls, FIGS. 10A-10H show embodiments of a system architecture for computers, including personal computers, to function within a network of computers, comprising: a computer with at least two microprocessors and having a connection means with a network of computers; the architecture for the computers including a firewall means for personal computers to limit access by the network to only a portion of the hardware, software, firmware, and other components of the personal computers; the firewall means does not permit access by the network to at least one microprocessor having a means to function as a master microprocessor to initiate and control the execution of a computer processing operation shared with at least one other microprocessor having a means to function as a slave microprocessor; and the firewall means permitting access by the network to the slave microprocessor. In addition, the system architecture explicitly includes embodiments of for example, the computer is a personal computer; the personal computer is a microchip; the computer have a control means by which to permit and to deny access to the computer by the network for shared computer processing; the system is scalar in that the system imposes no limit to the number of personal computers, including at least 256 said personal computers; the network is connected to the Internet and its equivalents and successors, so that the personal computers include at least a million personal computers; the system is scalar in that the system imposes no limit to the number of personal computers participating in a single shared computer processing operation, including at least 256 said personal computers; the personal computers having at least one microprocessor and communicating with the network through a connection means having a speed of data transmission that is preferably at least greater than a peak data processing speed of the microprocessor.

In summary, regarding the use of controllers with firewalls, FIGS. 10J-10M show embodiments of a system architecture for computers, including personal computers, to function within a network of computers, comprising for example: a computer with at least a controller and a microprocessor and having a connection means with a network of computers; the architecture for the computers including a firewall for personal computers to limit access by the network to only a portion of the hardware, software, firmware, and other components of the personal computers; the firewall does not permit access by the network to at least a one controller having a means to initiate and control the execution of a computer processing operation shared with at least one microprocessor having a means to function as a slave microprocessor; and the firewall permitting access by the network to the slave microprocessor. In addition, the system architecture explicitly includes embodiments of, for example, the computer is a personal computer; the personal computer is a microchip; the computer have a control means by which to permit and to deny access to the computer by the network for shared computer processing; the system is scalar in that the system imposes no limit to the number of personal computers, including at least 256 said personal computers; the network is connected to the Internet and its equivalents and successors, so that the personal computers include at least a million personal computers; the system is scalar in that the system imposes no limit to the number of personal computers participating in a single shared computer processing operation, including at least 256 said personal computers; the personal computers having at least one microprocessor and communicating with the network through a connection means having a speed of data transmission that is preferably at least greater than a peak data processing speed of the microprocessor; and the controller being capable of remote use.

In summary, regarding the use of firewalls that can be actively configured, FIGS. 10N-10Q show embodiments of a system architecture for computers, including personal computers, to function within a network of computers, comprising for example: a computer with at least two microprocessors and having a connection with a network of computers; the architecture for the computers including a firewall means for personal computers to limit access by the network to only a portion of the hardware, software, firmware, and other components of the personal computers; the firewall does not permit access by the network to at least a one microprocessor having a means to function as a master microprocessor to initiate and control the execution of a computer processing operation shared with at least one other microprocessor having a means to function as a slave microprocessor; the firewall permitting access by the network to the slave microprocessor; the configuration of the firewall being capable of change by a user or authorized local network administrator; the change in firewall configuration of a microchip PC is made at least in part using field-programmable gate arrays or equivalents or successors. In addition, the system architecture explicitly includes embodiments of, for example, the computer is a personal computer; the personal computer is a microchip; the computer have a control means by which to permit and to deny access to the computer by the network for shared computer processing; the system is scalar in that the system imposes no limit to the number of personal computers, including at least 256 said personal computers; the network is connected to the Internet and its equivalents and successors, so that the personal computers include at least a million personal computers; the system is scalar in that the system imposes no limit to the number of personal computers participating in a single shared computer processing operation, including at least 256 said personal computers; the personal computers having at least one microprocessor and communicating with the network through a connection means having a speed of data transmission that is preferably at least greater than a peak data processing speed of the microprocessor.

If the PC 1 microprocessors noted above are designed to the same basic consensus industry standard as parallel microprocessors for PC's (or equivalents or successors) as in FIGS. 10A-10B or for PC "systems on a chip" discussed in FIGS. 10C-10D, then although the cost per microprocessor can rise somewhat, especially initially, the net cost of computing for all users falls drastically almost instantly due to the general performance increase due to the use of otherwise idle "appliance" microprocessors. The potential very substantial benefit to all users should provide a powerful force to reach consensus on important industry hardware, software, and other standards on a continuing basis for such basic parallel network processing designs. If such basic industry standards are adopted at the outset and for the least number of shared microprocessors initially, and if design improvements incorporating greater complexity and more shared microprocessors are phased in gradually overtime on a step by step basis, then conversion to a MetaInternet architecture at all component levels should be relatively easy and inexpensive (whereas an attempt at sudden, massive conversion is hugely difficult and prohibitively expensive). The scalability of the MetaInternet system architecture (both vertically and horizontally) as described herein makes this sensible approach possible.

By 1998, manufacturing technology improvements allow 20 million transistors to fit on a single chip (with circuits as thin as 0.25 microns) and, in the next cycle, 50 million transistors using 0.18 micron circuits. Preferably, that entire computer on a chip is linked, preferably directly, by fiber optic or other broad bandwidth connection means so that the limiting factor on data throughput in the network system, or any part, is the speed of the linked microprocessors themselves.

For computers that are not reduced to a single chip, it is also preferred, but not mandatory for a substantial useful benefit, that the internal bus of any such PC's have a transmission speed that is at least high enough that the all processing operations of the PC microprocessor or microprocessors is unrestricted and that the microprocessor chip or chips are directly linked by fiber optic or other broad bandwidth connection, as with the system chip described above.

The individual user PC's can be connected to the Internet (via an Intranet)/Internet II/WWW or successor, like the MetaInternet (or other) network by any electromagnetic means, with the broad bandwidth speed of fiber optic cable being preferred, but hybrid systems using fiber optic cable for trunk lines and coaxial cable to individual users may be more cost effective initially, but less preferred unless cable can be made (through hardware and/or software and/or firmware and/or other component means) to provide sufficiently broad bandwidth connections to provide unrestricted throughput by connected microprocessors. Given the speed and bandwidth of transmission of fiber optic or equivalent connections, conventional network architecture and structures should be acceptable for good system performance, making possible a virtual complete interconnection network between users.

However, the best speed for any parallel processing operation should be obtained, all other things being equal, by utilizing the available microprocessors that are physically the closest together. Consequently, as shown previously in FIG. 8, the network needs have the means (through hardware and/or software and/or firmware and/or other component) to provide on a continually ongoing basis the capability for each PC to know the addresses of the nearest available PC's, perhaps sequentially, from closest to farthest, for the area or cell immediately proximate to that PC and then those cells of adjacent areas.

Figure 11:
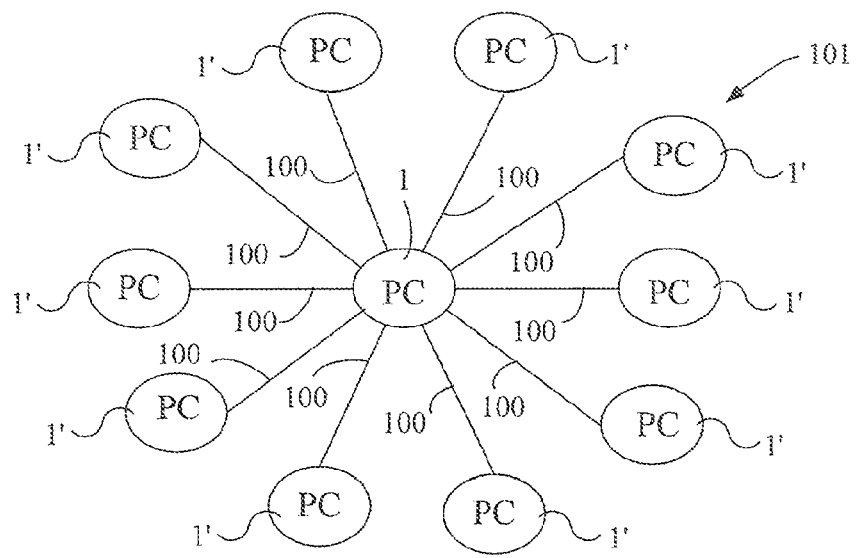
FIG. 11 is a simplified diagram of a section of a computer network, such as the Internet, showing an embodiment of a system architecture for connecting clusters of PC's to each other by wireless means, to create the closest possible (and therefore fastest) connections.

Network architecture that clusters PC's together should therefore be preferred, but not mandatory for substantial benefit, and can be constructed by wired means. However, as shown in FIG. 11, it is probably optimal to construct local network clusters 101 (or cells) of personal computers by wireless 100 means, since physical proximity of any PC 1 to its closest other PC 1' should be easier to access directly that way, as discussed further below. Besides, it is economically preferable for at least several network providers to serve any given geographic area to provide competitive service and prices.

Optimally, then, those wireless PC connections should be PC resident and capable of communicating by wireless or wired means with all available PC's in the cluster or cell geographic area, both proximal and potentially out to the practical limits of the wireless transmission.

Figure 12:
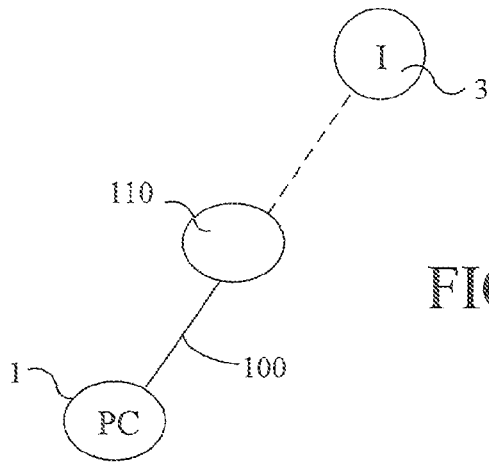
FIG. 12 is a simplified diagram of a section of a computer network, such as the Internet, showing an embodiment of a system architecture for connecting PC's to a satellite by wireless means.

As shown in FIG. 12, wireless PC connections 100 can be made to existing non-PC network components, such as one or more satellites 110, or present or future equivalent or successor components and the wireless transmissions can be conventional radio waves, such as infrared or microwave, or any other part of the electromagnetic wave spectrum.

Figure 13:
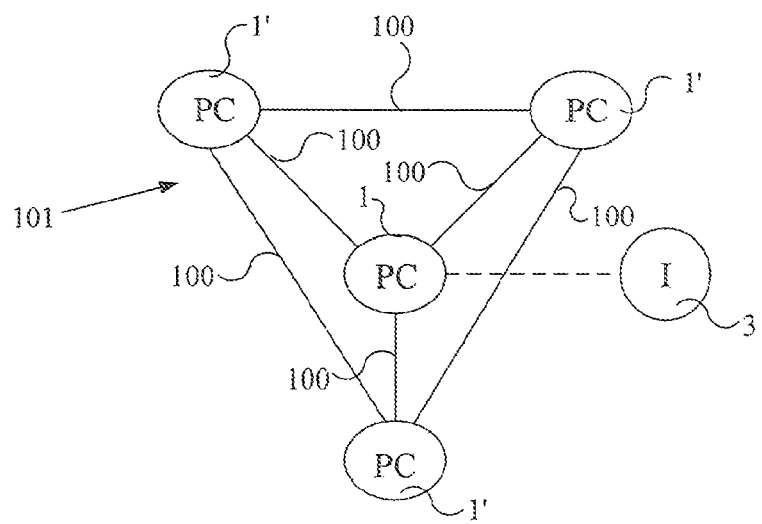
FIG. 13 is a simplified diagram of a section of a computer network, such as the Internet, showing an embodiment of a system architecture providing a cluster of networked PC's with complete interconnectivity by wireless means.

Moreover, as shown in FIG. 13, such a wireless or wired approach also make it easily possible in the future to develop network clusters 101 of available PC's 1' with complete interconnectivity; i.e., each available PC 1 in the cluster 101 is directly connected (preferably wirelessly 100) to every other available PC 1 in the cluster 101, constantly adjusting to individual PC's becoming available or unavailable. Given the speed of some wired broad bandwidth connections, like fiber optic cable, such clusters 101 with complete interconnectivity is certainly a possible embodiment.

As shown in FIG. 14A-14D, such wireless systems optimally include a wireless device 120 comprised of hardware and/or software and/or firmware and/or other component, like the PC 1 availability device described above preferably resident in the PC, but also with a network-like capability of measuring the distance from each PC 1 in its cluster 101 by that PC's signal transmission by transponder or its functional equivalent and/or other means to the nearest other PC's 1' in the cluster 101. As shown in FIG. 14A, this distance measurement could be accomplished in a conventional manner between transponder devices 120 connected to each PC in the cluster 101; for example, by measuring in effect the time delay from wireless transmission by the transponder device 120 of an interrogating signal 105 to request initiation of shared processing by a master PC 1 to the reception of a wireless transmission response 106 signaling availability to function as a slave PC from each of the idle PC's 1' in the cluster 101 that has received the interrogation signal 105. The first response signal 106' received by the master PC 1 is from the closest available slave PC 1" (assuming the simplest shared processing case of one slave PC and one master PC), which is selected for the shared processing operation by the requesting master PC 1, since the closer the shared microprocessor, the faster the speed of the wireless connections 100 is between sharing PC's (assuming equivalence of the connection means and other components among each of the PC's 1'). The interrogation signal 105 might specify other selection criteria also, for example, for the closest compatible (initially perhaps defined by a functional requirement of the system to be an identical microprocessor) slave PC 1", with the first response signal 106' being selected as above.

This same transponder approach also can be used between PC's 1" connected by a wired 99 means, despite the fact that connection distances is generally greater (since not line of sight, as is wireless), as shown in FIG. 14A, since the speed of transmission by the preferred broad bandwidth transmission means such as fiber optic cable is so high as to offset that greater distance. From a cost basis, this wired approach might be preferable for such PC's already connected by broad bandwidth transmission means, since additional wireless components like hardware and software are not necessary. In that case, the same transponder device 120 preferably is operated in wired clusters 101 in generally the same manner as described above for PC's connected in wireless clusters 101. Networks incorporating PC's 1 connected by both wireless and wired means are anticipated, like the home or business network mentioned in FIG. 10I, with mobile PC's or other computing devices preferably using wireless connections. Depending on distances between PC's and other factors, a local cluster 101 of a network 2 might connect wirelessly between PC's and with the network 2 through transponding means linked to wired broad bandwidth transmission means, as shown in FIG. 14C.

As shown in FIG. 14D, the same general transponder device means 120 can also be used in a wired 100 network system 2 employing network servers 98 operated, for example, by an ISP, or in other network system architectures (including client/server or peer to peer) or topologies (including ring, bus, and star) well known in the art or their future equivalents or successors.

The FIG. 14 approach to establishing local PC clusters 101 for parallel or other shared processing has major advantage in that it avoids using network computers such as servers (and, if wireless, other network components including even connection means), so that the entire local system of PC's within a cluster 101 operates independently of network servers, routers, etc. Moreover, particularly if connected by wireless means, the size of the cluster 101 could be quite large, being limited generally by PC transmission power, PC reception sensitivity, and local conditions. Additionally, one cluster 101 could communicate by wireless 100 means with an adjacent or other clusters 101, as shown in FIG. 14B, which could include those beyond its direct transmission range.

To improve response speed in shared processing involving a significant number of slave PC's 1, a virtual potential parallel processing network for PC's 1 in a cluster 101 preferably is established before a processing request begins. This is accomplished by the transponder device 120 in each idle PC 1, a potential slave, broadcasting by transponder 120 its available state when it becomes idle and/or periodically afterwards, so that each potential master PC 1 in the local cluster 101 is able to maintain relatively constantly its own directory 121 of the idle PC's 1 closest to it that are available to function as slaves. The directory 121 contains, for example, a list of about the standard use number of slave PC's 1 for the master PC (which initially probably is just one other PC 1") or a higher number, preferably listed sequentially from the closest available PC to the farthest. The directory of available slave PC's 1 is preferably updated on a relatively up to date basis, either when a change occurs in the idle state of a potential slave PC in the directory 121 or periodically.

Such ad hoc clusters 101 should be more effective by being less arbitrary geographically, since each individual PC is effectively in the center of its own ad hoc cluster. Scaling up or down the number of microprocessors required by each PC at any given time is also more seamless.

The complete interconnection potentially provided optimally by such ad hoc wireless clusters is also remarkable because such clusters mimics the neural network structure of the animal brain, wherein each nerve cell, called a neuron, interconnects in a very complicated way with the neurons around it. By way of comparison, the global network computer described above that is expected in a decade can have at least about 10 times as many PC's as a human brain has neurons and they can be connected by electromagnetic waves traveling at close to the speed of light, which is about 300,000 times faster than the transmission speed of human neurons (which, however, are much closer together).

An added note: in the next decade, as individual PC's become much more sophisticated and more network oriented, compatibility issues may recede to unimportance, since all major types of PC's will be able to emulate each other and most software, particularly relative to parallel processing, will no longer be hardware specific. Nearer term it will be important to set compatible hardware, software, firmware, and other component standards to achieve optimal performance by the components of the global network computer.

Until that compatibility is designed into the essential components of network system, the existing incompatibility of current components dramatically increase the difficulty involved in parallel processing across large networks. Programming languages like Java is one approach that will provide a partial means for dealing with this interim problem. In addition, using similar configurations of existing standards, like using PC's with a specific Intel Pentium chip with other identical or nearly identical components is probably the best way in the current technology to eliminate many of the serious existing problems that could easily be designed around in the future by adopting reasonable consensus standards for system components. The potential gains to all parties with an interest far outweigh the potential costs.

The above described global network computer system has an added benefit of reducing the serious and growing problem of nearly the immediate obsolescence of computer hardware, software, firmware, and other components. Since the preferred system above is the sum of its constituent parts used in parallel processing, each specific PC component becomes less critical. As long as access to the network utilizing sufficient bandwidth is possible, then all other technical inadequacies of the user's own PC can be completely compensated for by the network's access to a multitude of technically able PC's of which the user will have temporary use.

Although the global network computer will clearly cross the geographical boundaries of nations, its operation should not be unduly bounded by inconsistent or arbitrary laws within those states. There will be considerable pressure on all nations to conform to reasonable system architecture and operational standards generally agreed upon, since the penalty of not participating in the global network computer is potentially so high as to not be politically possible anywhere.

As shown in FIG. 15, because the largest number of user PC's are completely idle, or nearly so, during the night, it can be useful for the most complicated large scale parallel processing, involving the largest numbers of processors with uninterrupted availability as close together as possible, to be routed by the network to geographic areas of the globe undergoing night and to keep them there even as the Earth rotates by shifting computing resources as the world turns. As shown in FIG. 15, during the day, at least one parallel processing request by at least one PC 1 in a network 2 in the Earth's western hemisphere 131 are transmitted by very broad bandwidth connection wired 99 means such as fiber optic cable to the Earth's eastern hemisphere 132 for execution by at least one PC 1' of a network 2', which is idle during the night and the results are transmitted back by the same means to network 2 and the requesting at least one PC 1. Individual PC's within local networks like that operated by an ISP can be grouped into clusters or cells, as is typical in the practice of network industries. As is common in operating electrical power grids and telecommunications and computer networks, many such processing requests from many PC's and many networks could be so routed for remote processing, with the complexity of the system growing substantially over time in a natural progression.

This application encompasses all new apparatus and methods required to operate the above described network computer system or systems, including any associated computer or network hardware, software, or firmware (or other component), both apparatus and methods. Specifically included, but not limited to, are (in their present or future forms, equivalents, or successors): all enabling PC and network software and firmware operating systems, user interfaces and application programs; all enabling PC and network hardware design and system architecture, including all PC and other computers, network computers such as servers, microprocessors, nodes, gateways, bridges, routers, switches, and all other components; all enabling financial and legal transactions, arrangements and entities for network providers, PC users, and/or others, including purchase and sale of any items or services on the network or any other interactions or transactions between any such buyers and sellers; and all services by third parties, including to select, procure, set up, implement, integrate, operate and perform maintenance, for any or all parts of the foregoing for PC users, network providers, and/or others.

The combinations of the many elements the applicant's invention introduced in the preceding figures are shown because those embodiments are considered to be at least among the most useful possible, but many other useful combination embodiments are not shown simply because of the impossibility of showing them all, while at the same time maintaining a reasonable brevity in an unavoidably long description caused by the inherently highly connected nature of the inventions shown herein, which generally can operate all as part of one system of independently.

Therefore, any combination that is not explicitly described above is definitely implicit in the overall invention of this application and, consequently, any part of any of the preceding Figures and/or associated textual description can be combined with any part of any one or more other of the Figures and/or associated textual description of this application to create new and useful improvements over the existing art.

In addition, any unique new part of any of the preceding Figures and/or associated textual description can be considered by itself alone as an individual improvement over the existing art.

The forgoing embodiments meet the overall objectives of this invention as summarized above. However, it will be clearly understood by those skilled in the art that the foregoing description has been made in terms only of the most preferred specific embodiments. Therefore, many other changes and modifications clearly and easily can be made that are also useful improvements and definitely outside the existing art without departing from the scope of the present invention, indeed which remain within its very broad overall scope, and which invention is to be defined over the existing art by the appended claims.

The invention claimed is:

1. A computer comprising:
    a hardware master controlling device for the computer located on a microchip,
    one or more microprocessors;
    one or more hardware network communication components; and
    at least one internal hardware firewall located on said microchip;
        one said internal hardware firewall is configured to protect a hardware protected side of the computer's hardware and separate the hardware protected side of the computer's hardware from an unprotected network side that is not protected by said internal hardware firewall, said unprotected network side being configured to connect to a network of computers;
        at least said master controlling device is located within said hardware protected side of the computer; and
    one or more of said microprocessors and said one or more network communications components are located within said unprotected network side of the computer, and said unprotected network side of the computer being configured for connection to the network of computers and being located between said internal hardware firewall and a wired or wireless network connection to said network of computers,
        said one or more microprocessors located within said unprotected network side of the computer being separate components from said one or more network communications components, and both said microprocessors located within the unprotected network side and said one or more network communications components being separate from said internal hardware firewall.

2. The computer of claim 1, wherein the computer includes an active configuration of motherboard hardware.

3. The computer of claim 1, wherein said internal hardware firewall is also configured to make said hardware protected side of the computer inaccessible by a network; and
    said internal hardware firewall is configured to permit access by another computer in the network to said unprotected network side of the computer including said one or more microprocessors located within the unprotected network side.

4. The computer of claim 1, wherein said master controlling device for said computer includes a microprocessor.

5. The computer of claim 1, wherein said internal hardware firewall is also configured to deny access to said hardware protected side of the computer from said unprotected network side of the computer; and
    said internal hardware firewall is configured to permit access to said one or more microprocessors located within the unprotected network side of the computer.

6. The computer of claim 1, wherein the unprotected network side of the computer includes at least two microprocessors.

7. The computer of claim 1, wherein the unprotected network side of the computer includes at least four microprocessors.

8. The computer of claim 1, wherein said at least one network communications component includes at least a modem.

9. The computer of claim 1, wherein said internal hardware firewall denies access by said network to said hardware protected side of the computer.

10. The computer of claim 1, wherein said internal hardware firewall by its location does not restrict access by the network to the unprotected network side of the computer, thereby not restricting network operations conducted by the computer with the network, which are conducted in said unprotected network side using said network side microprocessors of the computer.

11. The computer of claim 1, wherein the hardware protected side includes at least a non-volatile memory and the unprotected network side includes at least a volatile memory.

12. The computer of claim 1, wherein the computer is configured to be a personal computer or a node in an array of other said computers as nodes linked together to form a server and/or a mainframe and/or a supercomputer.

13. The computer of claim 1, wherein said computer is configured to at least perform Internet browsing with the network of computers, and said Internet browsing is executed at least by said at least one microprocessor located in said unprotected network portion of the computer.

14. The computer of claim 1, wherein said microchip is configured for use by at least one individual user, and
    wherein at least one of said hardware network communications components and said one or more microprocessors located within said unprotected network side are located on said microchip.

15. The computer of claim 1, wherein said unprotected network side includes at least one of the following components: active configuration of one or more integrated circuits, sound, hard drive, optical disk drive, or video or other display components.

16. The computer of claim 1, wherein said one or more microprocessors located within said unprotected network side of the computer are located on said microchip.

17. The computer of claim 1, wherein said one or more hardware network communication components are located on said microchip.

18. The computer of claim 1, comprising at least two hardware network communications components.

19. The computer of claim 1, wherein said microchip includes active configuration of one or more integrated circuits.

20. The computer of claim 1, wherein said microchip includes one or more field programmable gate arrays (FPGA).

21. A computer comprising:
    two or more microprocessors;
    at least one hardware network communications component; and
    at least one internal hardware firewall located on a microchip;
        one said internal hardware firewall is configured to protect a hardware protected side of the computer's hardware and separate the hardware protected side of the computer's hardware from an unprotected network side of the computer's hardware that is not protected by said internal hardware firewall, said unprotected network side being configured to connect to a network of computers;
        at least one said microprocessor is located on said microchip and within said hardware protected side of the computer that is protected by at least said internal hardware firewall;
        one or more of said microprocessors and said at least one network communications component are located within said unprotected network side that is located between said internal hardware firewall and a wired or wireless network connection, said one or more microprocessors located within said unprotected network side of the computer being separate components from said at least one network communications component, and both said microprocessors located within the unprotected network side and said at least one network communications component being separate from said internal hardware firewall.

22. The computer of claim 21, wherein the computer includes an active configuration of motherboard hardware.

23. The computer of claim 21, wherein said internal hardware firewall is configured to deny access to said hardware protected side of the computer by a network; and said internal hardware firewall is also configured to permit access by another computer in the network to said unprotected network side of the computer including said one or more microprocessors located within the unprotected network side.

24. The computer of claim 21, wherein said internal hardware firewall is also configured to deny access to said hardware protected side of the computer from said unprotected network side of the computer; and said internal hardware firewall is also configured to permit access to said one or more unprotected microprocessors located within the unprotected network side of the computer.

25. The computer of claim 21, wherein the unprotected network side includes at least two microprocessors.

26. The computer of claim 21, wherein the unprotected network side includes at least four microprocessors.

27. The computer of claim 21, wherein said at least one network communications component includes at least a modem.

28. The computer of claim 21, wherein said internal hardware firewall denies access by said network to said hardware protected side of the computer.

29. The computer of claim 21, wherein said internal hardware firewall by its location does not restrict access by the network to the unprotected network side of the computer, thereby not restricting network operations conducted by the computer with the network, which are conducted in said unprotected network side using said network side microprocessors of the computer.

30. The computer of claim 21, wherein the hardware protected side includes at least a non-volatile memory and the unprotected network side includes at least a volatile memory.

31. The computer of claim 21, wherein the computer is configured to be a personal computer or a node in an array of other said computers as nodes linked together to form a server and/or a mainframe and/or a supercomputer.

32. The computer of claim 21, wherein said computer is configured to at least perform Internet browsing with the network of computers, and said Internet browsing is executed at least by said at least one microprocessor located in said unprotected network portion of the computer.

33. The computer of claim 21, wherein said microchip is configured for use by at least one individual user, and wherein at least one of said hardware network communications components and said one or more microprocessors located within said unprotected network side are located on said microchip.

34. The computer of claim 21, wherein said unprotected network side includes at least one of the following components: active configuration of one or more integrated circuits, sound, hard drive, optical disk drive, or video or other display components.

35. The computer of claim 21, wherein said one or more microprocessors located within said unprotected network side of the computer are located on said microchip.

36. The computer of claim 21, wherein said one or more hardware network communication components are located on said microchip.

37. The computer of claim 21, wherein said microchip includes active configuration of one or more integrated circuits.

38. The computer of claim 21, wherein said microchip includes one or more field programmable gate arrays (FPGA).

39. The computer of claim 21, comprising at least two hardware network communications components.

40. A microchip, comprising:

a microprocessor, the microprocessor including at least two processing units;

at least one network communications component; and at least one internal hardware firewall;

one said internal hardware firewall is configured to separate a hardware protected side of the microchip's hardware from an unprotected network side of the microchip's hardware, said unprotected network side being configured for connection to a network;

at least one of the processing units of the microprocessor is located within said hardware protected side that is protected by at least said internal hardware firewall; and one or more of the processing units of the microprocessor and said at least one network communications component is located within said unprotected network side that is located between said internal hardware firewall and a wired or wireless network connection, said one or more unprotected network side processing units being separate components from said at least one network communications component, and both said unprotected network side processing units and said at least one network communications component being separate from said internal hardware firewall.

41. The microchip of claim 40, wherein the microchip includes an active configuration of the integrated circuits of the microchip in the form of at least one microcircuit electromechanical switch or lock.

42. The microchip of claim 40, wherein said internal hardware firewall is configured to deny access to said hardware protected side of the microchip by a network; and said internal hardware firewall is also configured to permit access by another computer in the network to said one or more network side processing units included in the unprotected network side of the microchip.

43. The microchip of claim 40, wherein said at least one processing unit included in said hardware protected side of the microchip includes a master control unit.

44. The microchip of claim 40, wherein said internal hardware firewall is configured to deny access to said hardware protected side of the microchip from said unprotected network side of the microchip; and said internal hardware firewall is also configured to permit access to said one or more network side processing units included in the unprotected network side of the microchip.

45. The microchip of claim 40, wherein the unprotected network side of the microchip includes at least two processing units.

46. The microchip of claim 40, wherein the unprotected network side of the microchip includes at least four processing units.

47. The microchip of claim 40, wherein said at least one network communications component includes at least a modem.

48. The microchip of claim 40, wherein said internal hardware firewall denies access by said network to said hardware protected side of the microchip.

49. The microchip of claim 40, wherein said internal hardware firewall by its location does not restrict access by the network to the unprotected network side of the microchip, thereby not restricting network operations conducted by the microchip with the network, which are conducted in said unprotected network side using said network side processing units of the microchip.

50. The microchip of claim 40, wherein the hardware protected side includes at least a non-volatile memory and the unprotected network side includes at least a volatile memory.

51. The microchip of claim 40, wherein the microchip is included in a computer configured to be a personal computer or a node in an array of other said computers as nodes linked together to form a server and/or a mainframe and/or a supercomputer.

52. The microchip of claim 40, wherein said microchip is configured to at least perform Internet browsing with the network of computers, and said Internet browsing is executed at least by said at least one processing unit located in said unprotected network portion of the microchip.

53. The microchip of claim 40, wherein said microchip further includes a graphics component.

54. The microchip of claim 40, wherein said microchip further includes a field programmable gate array.

55. The microchip of claim 40, wherein said unprotected network side includes at least one of the following components: active configuration of one or more integrated circuits, sound or video processing components.

56. The microchip of claim 40, comprising at least two hardware network communications components.

57. A microchip, comprising:
a microprocessor, the microprocessor including at least two processing units;
one or more field programmable gate arrays (FPGA); and
at least one internal hardware firewall;
one said internal hardware firewall is configured to separate a hardware protected side of the microchip's hardware from an unprotected network side of the microchip's hardware, said unprotected network side being configured for connection to a network;
at least one of the processing units of the microprocessor is located within said hardware protected side that is protected by at least said internal hardware firewall; and
one or more of the processing units of the microprocessor and said one or more field programmable gate arrays (FPGA); are located within said unprotected network side that is located between said internal hardware firewall and a wired or wireless network connection,
said one or more network side processing units being separate components from said one or more field programmable gate arrays (FPGA);, and both said network side processing units and one or more said field programmable gate arrays (FPGA); being separate from said internal hardware firewall.

58. The microchip of claim 57, wherein said at least one processing unit included in said hardware protected side of the microchip includes a master control unit.

59. The microchip of claim 57, wherein said internal hardware firewall denies access by said network to said hardware protected side of the microchip.

60. The microchip of claim 57, wherein said internal hardware firewall by its location does not restrict access by the network to the unprotected network side of the microchip, thereby not restricting network operations conducted by the microchip with the network, which are conducted in said unprotected network side using said network side processing units of the microchip.

61. The microchip of claim 57, comprising at least two hardware network communications components.

* * * * *